(12) United States Patent
Nakamura et al.

(10) Patent No.: US 8,145,440 B2
(45) Date of Patent: Mar. 27, 2012

(54) BODY DYNAMICS CALCULATION METHOD, BODY DYNAMICS MODEL AND MODEL DATA THEREOF, AND BODY-MODEL GENERATION METHOD

(75) Inventors: Yoshihiko Nakamura, Tokyo (JP); Katsu Yamane, Saitama (JP); Ichiro Suzuki, Tokyo (JP); Kazutaka Kurihara, Tokyo (JP); Koji Tatani, Kanagawa (JP)

(73) Assignee: Japan Science and Technology Agency (JP)

( * ) Notice: Subject to any disclaimer, the term of this patent is extended or adjusted under 35 U.S.C. 154(b) by 487 days.

(21) Appl. No.: 12/348,461

(22) Filed: Jan. 5, 2009

(65) Prior Publication Data

US 2009/0132217 A1 May 21, 2009

Related U.S. Application Data

(62) Division of application No. 10/519,019, filed as application No. PCT/JP03/06344 on May 21, 2003, now Pat. No. 7,490,012.

(30) Foreign Application Priority Data

May 29, 2002 (JP) ................................. 2002-154853
Jun. 6, 2002 (JP) ................................. 2002-165234

(51) Int. Cl.
*G01L 1/00* (2006.01)

(52) U.S. Cl. ........................................................ 702/41

(58) Field of Classification Search .................... 702/41; 606/102; 700/63; 600/416; 703/6, 7; 345/473; 434/262
See application file for complete search history.

(56) References Cited

U.S. PATENT DOCUMENTS

| | | | |
|---|---|---|---|
| 6,161,080 A * | 12/2000 | Aouni-Ateshian et al. ...... 703/11 |
| 7,184,814 B2 * | 2/2007 | Lang et al. .................... 600/416 |
| 2004/0167641 A1 * | 8/2004 | Kawai et al. ................... 700/63 |
| 2005/0101966 A1 * | 5/2005 | Lavallee ...................... 606/102 |

* cited by examiner

*Primary Examiner* — Drew A Dunn
*Assistant Examiner* — Xiuquin Sun
(74) *Attorney, Agent, or Firm* — Lowe Hauptman Ham & Berner, LLP

(57) ABSTRACT

A forward/reverse mechanics calculation of an accurate model of a human body having bone geometrical data and muscle/cord/band data is carried out at high speed. When a new skeleton geometrical model is given, a mapping between the new skeleton geometrical model and a pre-defined normal body model representing a normal body is defined to automatically produce a new body model. A processing unit reads model data to be subjected to mechanics calculation, reads a produced force f of a wire/virtual link exerted on the body model, reads the angle, position and velocity of the current rigid body link, calculates the Jacobian $J_L$ of the length of each wire concerning the joint angle, converts the read produced force f of the muscle/cord/band into a generalized force $\tau_G$ according to the defined Jacobian $J_L$, stores the generalized force, determines the acceleration of the whole body of a motion produced when the generalized force $\tau_G$ is exerted on the body and calculates the velocity and position of each rigid body link, and stores them.

17 Claims, 24 Drawing Sheets

```
DEF node_name Transform {
    translation x y z
    rotation x y z w
```

FIG.10

```
world
        bones                               # BONE
            bone1
            bone2
        virtual_bones                       # VIRTUAL LINK
            virtual_bone1
        muscles                             # MUSCLE
            C_Mus_muscle1
                C_Mus_muscle1_Org_bone1     # ORIGIN
                C_Mus_muscle1_End_bone2     # END POINT
            L_Mus_muscle2
                L_Mus_muscle2_Org_bone2
                L_Mus_muscle2_End_virtual_bone1
                L_Mus_muscle2_1_bone2       # VIA-POINT 1
                L_Mus_muscle2_2_bone2       # VIA-POINT 2
        tendons                             # TENDON
            L_Ten_tendon1
                L_Ten_tendon1_Org_virtual_bone1
                L_Ten_tendon1_End_bone2
        ligamenta                           # LIGAMENT
            R_Lig_lig1
                R_Lig_lig1_Org_bone1
                    R_Lig_lig1_End_virtual_bone1
```

FIG. 11

BODY DYNAMICS CALCULATION METHOD, BODY DYNAMICS MODEL AND MODEL DATA THEREOF, AND BODY-MODEL GENERATION METHOD

CROSS-REFERENCE TO RELATED APPLICATIONS

The present application is a Divisional of U.S. patent application Ser. No. 10/515,019, filed Aug. 30, 2005 and issued U.S. Pat. No. 7,490,012 on Feb. 10, 2009, which in turn is based on International Application No. PCT/JP03/06344, filed May 21, 2003, which in turn corresponds to Japanese Application Nos. JP 2002-154853, filed May 29, 2002 and JP 2002-165234, filed Jun. 6, 2002, and priority is hereby claimed under 35 USC §119 based on these applications. Each of these applications are hereby incorporated by reference in their entirety into this application.

TECHNICAL FIELD

The present invention relates to body dynamics calculation methods, body dynamics calculation programs, recording media having recorded thereon the programs, body dynamics models, and recording media having stored thereon the model data of the models, for muscles, tendons, ligamenta, and skeletons. The present invention particularly relates to a model of a skeleton and a model of muscles, tendons, and ligamenta, both model being used as a basis for kinematics analysis and dynamics analysis based on a precise model of a body, such as a human body, an animal body, or a living body, and also to a dynamics calculation method for the model of muscles, tendons, and ligamenta, used for such analysis.

The present invention also relates to body-model generation methods, body-model generation programs, recording media having stored thereon the generation programs, and recording media having recorded thereon body-model data. The present invention can be applied to fields, such as those for systems for generating a model of a body, such as a human body or a living body, and for data bases of a model of a body, such as a human body or a living body.

The present invention can also be applied to the following example technologies.

(1) Motion analysis software for a model of a body, such as a human body or a living body (2) Motion generation software for a model of a body, such as a human body or a living body (3) Wire-driving-mechanism motion analysis software (4) Wire-driving-mechanism control software

BACKGROUND ART

In the cognitive science and the medical field, the need for kinematics analysis and dynamics analysis based on a precise human-body model has been increasing. To conduct research on information processing in brain in the cognitive science, for example, information close to a human body, such as force applied to a joint and force generated by a muscle or a ligament, is necessary. In orthopedics, quantitative planning for an operation method which allow the motor function to be most recovered is an issue. To this end, precise analysis and simulation are required based on the shapes of muscles and bones.

The following references 1 to 3 include cases in which an attempt to model a human body precisely was made and motion analysis was performed with the use of the model. Especially in reference 2, kinematics analysis was performed to calculate a change in muscle length, and the change was applied to a physiological model of muscles to calculate muscular strength. In reference 3, muscular strength was calculated from the motion of a model.

(Reference 1)

Suzuki, Hattori, Tominaga, and Urano, "Manufacturing and Applications of Highly-Functional Multi-Purpose Three-Dimensional Model (digital dummy) (second report)," presented at the 18th IPA Technical Meeting, 1999.

(Reference 2)

Suzuki and Tominaga, "Manufacturing and Applications of Highly-Functional Multi-Purpose Three-Dimensional Model (digital dummy) (third report)," presented at the 19th IPA Technical Meeting, 2000.

(Reference 3)

M. G. Pandy and F. C. Anderson, "Dynamic Simulation of Human Movement Using Large-Scale Models of the Body," Proc. IEEE Intl. Conf. Robotics and Automation, pp. 676-681, 2000. (Dynamics analysis of a dynamics model of a human body, including muscles)

As described above, attempts to model a human body precisely have been conventionally performed, but complicated muscles and ligamenta having a great number of edge points cannot be sufficiently correctly modeled. Modeling is mainly performed for kinematics analysis, and just a few models can be used for dynamics calculation. Since researchers use their own formats, it is difficult to accumulate and re-use data and to make a data base thereof.

As described above, motion analysis was performed in some cases with the use of a precise model of a human body, including muscles, tendons, and ligamenta, but a method for performing at high speed forward (calculating motion from muscular strength) and inverse (calculating muscular strength from motion) dynamics calculation. In addition, in conventional dynamics calculation, since a complicated optimization problem is solved, a long calculation time is required irrespective of a relatively simple model. Further, forward dynamics calculation was conventionally not performed.

The above issues have been considered, and an object of the present invention is to provide a body dynamics model of a skeleton, muscles, tendons, and ligamenta which form a body, such as a human body or a living body, with as high fidelity as possible and in a usable form for kinematics and dynamics calculation, and a computer-readable recording medium having accumulated thereon body-dynamics-model data in a uniform format so as to configure a data base thereof.

Another object of the present invention is to provide a body dynamics calculation method, a body dynamics calculation program, and a recording medium having recorded thereon the program, for performing at high speed forward-dynamics calculation (calculating motion from muscle strength) and inverse-dynamics calculation (calculating muscle strength from motion) for a detailed body model which includes a skeleton, and muscles, tendons, and ligamenta, Methods for configuring detailed human-body models which include bones, muscles, tendons, and ligamenta, from medical data such as that obtained by MRI/CT have been conventionally proposed. Since such a model generally includes several hundreds of muscles, tendons, and ligamenta, data generation needs much time and labor, and it is unrealistic to generate models of a plurality of test subjects.

The above-described issue has been considered, and an object of the present invention is to provide a body-model generation method, a body-model generation program, a recording medium having recorded thereon the program, and a recording medium having recorded thereon body-model data, all used for automatically generating a new body model by mapping with a standard body model indicating a standard body defined in advance, when a new geometric skeletal model is given.

To perform calculation of precise analysis and simulation based on the shapes of muscles and bones, it is necessary to obtain detailed human-body models which includes muscles, tendons, and ligamenta, of a great number of test subjects. Since several hundreds of muscles, tendons, and ligamenta are required for one person, data generation needs much labor. An object of the present invention is to provide a technology for mapping information of muscles, tendons, and ligamenta in a standard detailed model onto a bone geometric model so as to save labor for generating a detailed model.

DISCLOSURE OF INVENTION

The present invention provides a united and effective method for modeling kinematics action and dynamics action of muscles, tendons, and ligamenta inside a computer to facilitate the generation of a detailed model. In addition, the present invention provides specifications for storing the detailed model in a file to allow the detailed model to be used for data-base generation and to be used mutually among applications.

Further, the present invention performs conversion between generalized forces in a link system and the forces of muscles, tendons, and ligamenta modeled in wire according to a body dynamics model of muscles, tendons, and ligamenta to allow calculation methods such as a link-system dynamics high-speed calculation method to be applied to implement high-speed dynamics calculation.

According to the first solving means of the present invention there are provided, a dynamics calculation method for muscles, tendons, ligamenta, and a skeleton, a dynamics calculation program for muscles, tendons, ligamenta, and a skeleton for making a computer execute each of the foregoing steps, and a recording medium having stored thereon the program, for calculating, in a body model defined by data for rigid links expressing a skeleton and data for wires/virtual links expressing muscles, tendons, and ligamenta, the motion of the rigid links from forces applied to or generated by the wires/virtual links, the dynamics calculation method or program comprising:

a step of reading model data which includes the shapes and dynamics data of the wires/virtual links and the rigid links for which dynamics calculation is performed, from a model-data file by a processing section;

a step of reading generation forces f applied to or generated by the wires/virtual links from a generation-force file by the processing section, the generation forces being given to the body model;

a step of reading the current angles, positions, and velocities of the rigid links from a rigid-link file having stored the angles, positions, and velocities of the rigid links, by the processing section;

a step of calculating a Jacobian $J_L$ for the joint angle of the length of each wire according to the model data and the angles, positions, and velocities of the rigid links, by the processing section;

a step of converting the read generation forces f of muscles, tendons, and ligamenta into generalized forces $\tau_G$ serving as forces at the connection points of the rigid links, according to the obtained Jacobians $J_L$ by the following equation, by the processing section;

$$\tau_G = J_L^T f$$

a step of storing the obtained generalized forces $\tau_G$ in a generalized-force file, by the processing section;

a step of obtaining the acceleration of the rigid links in the whole body for the motion generated as a result of receiving the generalized force $\tau_G$ according to the generalized forces $\tau_G$ and the current angles and velocities of the rigid links, and then of calculating the velocity and position of each rigid link according to the obtained acceleration, by the processing section; and a step of storing the obtained angles, positions, and velocities of the rigid links in a rigid-link file.

According to the second solving means of the present invention there are provided, a dynamics calculation method for muscles, tendons, ligamenta, and a skeleton, a dynamics calculation program for muscles, tendons, ligamenta, and a skeleton for making a computer execute each of the foregoing steps, and a recording medium having stored thereon the program, for calculating, in a body model defined by data for rigid links expressing a skeleton and data for wires/virtual links expressing muscles, tendons, and ligamenta, forces applied to or generated by the wires/virtual links from acceleration given to the rigid links, the dynamics calculation method or program comprising:

a step of reading model data which includes the shapes and dynamics data of the wires/virtual links and the rigid links for which dynamics calculation is performed, from a model-data file by a processing section;

a step of reading the current angles, positions, and velocities of the rigid links from a rigid-link file having stored the angles, positions, and velocities of the rigid links, and also of reading acceleration given to the rigid links from an acceleration file, by the processing section;

a step of calculating a Jacobian $J_L$ for the joint angle of the length of each wire according to the model data and the angles, positions, and velocities of the rigid links, by the processing section;

a step of calculating generalized forces $\tau_G$ serving as forces at the connection points of the rigid links, required for generating motion caused by the acceleration given to the rigid links, according to the acceleration of the rigid links read from the acceleration file and the angles and velocities read from the rigid-link file, by the processing section;

a step of storing the obtained generalized forces $\tau_G$ in a generalized-force file, by the processing section;

a step of solving the following equation for f according to the previously obtained $J_L$ to obtain the generation forces f applied to each wire/virtual link from the generalized forces $\tau_G$, by the processing section;

$$\tau_G = J_L^T f$$

and a step of storing the obtained rigid-link generation forces f in a generation-force file.

According to the third solving means of the present invention there is provided, a dynamics calculation method for muscles, tendons, ligamenta, and a skeleton, for calculating a Jacobian $J_L$ for the joint angle of the length of a wire, in a body model defined by data for rigid links expressing a skeleton and data for wires/virtual links expressing muscles, tendons, and ligamenta, according to model data which includes the shapes and dynamics data of the wires/virtual links and the rigid links for which dynamics calculation is performed, and data of the angles, positions, and velocities of the rigid links, the dynamics calculation method comprising:

(1) a step of calculating the wire length $l_i$ and the positions $p_{i,j}$ of the via-point and the edge points of a wire i from the model data and the current angles, positions, and velocities of the rigid links, by the processing section;

(2) a step of calculating a Jacobian $J_{p_{i,j}}$ for the joint angle $\theta_G$ of the positions $p_{i,j}$ to calculate a Jacobian $J_{L_{i,j}}$ for the joint angle $\theta_G$ of a distance $l_{i,j}$ by the following equation by the processing section;

$$J_{Li,j}=l_{i,j}^{-1}(p_{i,j+1}-p_{i,j})^T(J_{pi,j+1}-J_{pi,j})$$

(3) a step of calculating $J_{Li}$ by the total sum of the obtained $J_{Li,j}$ for j by the processing section; and (4) a step of obtaining the Jacobian $J_L$ by collecting $J_{Li}$ to obtain $J_L = [J_{L1} \ J_{L2} \ldots J_{Li} \ldots]$, where the wire i comprises $m_i$ via-points and edge points, $l_{i,j}$ indicates the distance from a via-point or edge point j to a via-point or edge point j+1, $p_{i,j}$ indicates the position of a via-point or edge point j, $\theta_G$ indicates the joint angle, and $\theta_G'$ indicates the angular velocity of the joint.

According to the forth solving means of the present invention there is provided, a body dynamics model for muscles, tendons, ligamenta, and a skeleton, expressed by data for wires and virtual links connected between the wires which express muscles, tendons, and ligamenta of a body which includes a human body, a living body, or an animal body, and data for rigid links which express bones, wherein a plurality of the rigid links are coupled by joints which express joints having a plurality of degrees of freedom to form a skeleton;

the wires connect origins and end points secured to predetermined locations of the bones expressed by the rigid links, pass through no or one or more via-points which allow sliding and are secured to bones, and are formed such that the lengths and tension of the wires can be changed according to the movement of the rigid links;

the virtual links are formed such that the origins and end points of a plurality of the wires are secured; and forces applied to the wires and the virtual links, the lengths of the wires, and the motion of the rigid links interact with each other.

According to the fifth solving means of the present invention there is provided, a computer-readable recording medium having stored thereon body-dynamics-model data for muscles, tendons, ligamenta, and a skeleton, in which the muscles, tendons, and ligamenta are expressed by wires and virtual links connected between the wires and bones are expressed by rigid links, in a body which includes a human body, a living body, or an animal body, wherein the body-dynamics-model data comprises:

rigid-link data comprising shape data of the rigid links a plurality of which are coupled with each other by joints which express joints having a plurality of degrees of freedom to form a skeleton, and dynamics data comprising the mass, inertial moment, and the center of mass of each rigid link, position data of the edge points and/or via-points of the wires, the wires connecting origins and end points secured to predetermined locations of the bones expressed by the rigid—link data, passing through no or one or more via-points which allow sliding and are secured to the bones, and being formed such that the lengths and tension of the wires can be changed according to the movement of the rigid links, and shape data and position data of the virtual links to which the origins and end points of a plurality of the wires are secured; and forces applied to the wires and/or the virtual links, the lengths of the wires, and the motion of the rigid links interact with each other.

According to the sixth solving means of the present invention there are provided, a body-model generation method, a body-model generation program for making a computer execute each of the foregoing steps, and a computer-readable recording medium having stored thereon the program, for generating, according to a standard body model which expresses a skeletal model and a model of muscles, tendons, and ligamenta of a standard body, a new body model by mapping the model of muscles, tendons, and ligamenta onto a new skeletal model which expresses the skeleton of a new body, comprising:

a step of inputting by the processing section from a standard-body-model file stored in a storage section, standard-body-model data which defines the standard body model by standard-skeletal-model data for rigid links expressing the geometric shape of a skeleton, and standard-model data for muscles, tendons, and ligamenta, when the muscles, tendons, and ligamenta are expressed by wires and virtual links connected between the wires, for the virtual links and the origins, end points, and via-points of the wires;

a step of inputting by the processing section from a new-body-model file stored in the storage section, new-skeletal-model data which defines the new skeletal model measured or given in advance of the new body model, by data for the rigid links expressing the geometric shape of the skeleton;

a step of making an input section arrange or automatically extracting a plurality of feature points on or from each rigid link according to the input standard-skeletal-model data, by the processing section;

a step of making the input section arrange or automatically extracting a feature point corresponding to each feature point of the standard-skeletal-model data on or from each rigid link according to the input new-skeletal-model data, by the processing section;

a step of associating the obtained feature points of the standard-skeletal-model data with the obtained feature points of the new-skeletal-model data and storing them in a feature-point file, by the processing section;

a step of applying optimization calculation to a value corresponding to the sum of or the sum of the squares of the distances between the corresponding feature points to obtain the parameters of conversions which include parallel movement, rotational movement, and scaling, and of storing the conversion parameters into a conversion-parameter file, by the processing section;

a step of specifying a coordinate system for the input new skeletal model so as to fit the coordinate system of the standard skeletal model, by the processing section; and a step of mapping the data of the standard model of muscles, tendons, and ligamenta for the virtual links and the positions of the origins, the end points, and via-points of the wires in the standard skeletal model onto the new skeletal model according to the conversion parameters read from the conversion-parameter file to obtain data of the new model of muscles, tendons, and ligamenta for virtual links and the absolute positions of the origins, end points, and via-points of muscles, tendons, and ligamenta in the coordinate system of the new skeletal model, and of storing the data into the new-body-model file, by the processing section.

According to the seventh solving means of the present invention there are provided, a body-model generation method, a body-model generation program for making a computer execute each of the foregoing steps, and a computer-readable recording medium having stored thereon the program, for generating, according to a standard body model which expresses a skeletal model and a model of muscles, tendons, and ligamenta of a standard body, a new body model by mapping the model of muscles, tendons, and ligamenta onto a new skeletal model which expresses the skeleton of a new body, comprising:

a step of inputting by the processing section from a standard-body-model file stored in a storage section, standard-body-model data which defines the standard body model by standard-skeletal-model data for rigid links expressing the geometric shape of a skeleton, and standard-model data for muscles, tendons, and ligamenta, when the muscles, tendons, and ligamenta are expressed by wires, for the origins, end points, and via-points or for the origins and end points of the wires;

a step of inputting by the processing section from a new-body-model file stored in the storage section, new-skeletal-model data which defines the new skeletal model measured or given in advance of the new body model, by data for the rigid links expressing the geometric shape of the skeleton;

a step of making an input section arrange or automatically extracting a plurality of feature points on or from each rigid link according to the input standard-skeletal-model data, by the processing section;

a step of making the input section arrange or automatically extracting a feature point corresponding to each feature point of the standard-skeletal-model data on or from each rigid link according to the input new-skeletal-model data, by the processing section;

a step of associating the obtained feature points of the standard-skeletal-model data with the obtained feature points of the new-skeletal-model data and storing them in a feature-point file, by the processing section;

a step of applying optimization calculation to a value corresponding to the sum of or the sum of the squares of the distances between the corresponding feature points to obtain the parameters of conversions which include parallel movement, rotational movement, and scaling, and of storing the conversion parameters into a conversion-parameter file, by the processing section;

a step of specifying a coordinate system for the input new skeletal model so as to fit the coordinate system of the standard skeletal model, by the processing section; and a step of mapping the data of the standard model of muscles, tendons, and ligamenta for the positions of the origins, end points, and via-points, or the origins and end points of the wires in the standard skeletal model onto the new skeletal model according to the conversion parameters read from the conversion-parameter file to obtain data of the new model of muscles, tendons, and ligamenta for the absolute positions of the origins, end points, and via-points, or the origins and the end points of muscles, tendons, and ligamenta in the coordinate system of the new skeletal model, and of storing the data into the new-body-model file, by the processing section.

According to the eighth solving means of the present invention there is provided, a computer-readable recording medium having stored thereon a standard-body-model data used for generating, according to a standard body model which expresses a skeletal model and a model of muscles, tendons, and ligamenta of a standard body, a new body model by mapping the model of muscles, tendons, and ligamenta onto a new skeletal model which expresses the skeleton of a new body, the standard-body-model data having a standard-skeletal-model data structure for rigid links expressing the geometric shape of a skeleton, and a standard-model data structure for muscles, tendons, and ligamenta, when the muscles, tendons, and ligamenta are expressed by wires and virtual links connected between wires, for the virtual links and the origins, end points, and via-points of the wires, and defining the standard body model, and the processing section (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the virtual links and the positions of the origins, end points, and via-points of the wires in the standard skeletal model onto the new skeletal model to obtain data of the new model of muscles, tendons, and ligamenta for virtual links and the origins, end points, and via-points of muscles, tendons, and ligamenta in the coordinate system of the new skeletal model.

According to the ninth solving means of the present invention there is provided, a computer-readable recording medium having stored thereon a standard-body-model data used for generating, according to a standard body model which expresses a skeletal model and a model of muscles, tendons, and ligamenta of a standard body, a new body model by mapping the model of muscles, tendons, and ligamenta onto a new skeletal model which expresses the skeleton of a new body, the standard-body-model data having a standard-skeletal-model data structure for rigid links expressing the geometric shape of a skeleton, and a standard-model data structure for muscles, tendons, and ligamenta, when the muscles, tendons, and ligamenta are expressed by wires, for the origins, end points, and via-points, or for the origins and end points of the wires, and defining the standard body model, and the processing section (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the positions of the origins, end points, and via-points, or the origins and end-points of the wires in the standard skeletal model onto the new skeletal model to obtain data of the new model of muscles, tendons, and ligamenta for the origins, end points, and via-points, or the origins and end points of muscles, tendons, and ligamenta in the coordinate system of the new skeletal model.

According to the tenth solving means of the present invention there is provided, a computer-readable recording medium having stored thereon a new-body-model data generated by mapping, according to a standard body model which expresses a skeletal model and a model of muscles, tendons, and ligamenta of a standard body, the model of muscles, tendons, and ligamenta onto a new skeletal model which expresses a new body, the new-body-model data having a standard-skeletal-model data structure for rigid links expressing the geometric shape of a skeleton, and a new-model data structure for muscles, tendons, and ligamenta, when the muscles, tendons, and ligamenta are expressed by wires and virtual links connected between the wires, for the virtual links and the origins, end points, and via-points of the wires, and defining a new body model, the standard-body-model data defining the standard body model by a standard-skeletal-model data for rigid links expressing the geometric shape of a skeleton, and a standard-model data structure for muscles, tendons, and ligamenta, when the muscles, tendons, and ligamenta are expressed by wires and virtual links connected between the wires, for the virtual links and the origins, end points, and via-points of the wires, and the processing section (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the virtual links and the positions of the origins, end points, and via-points of the wires in the standard skeletal model onto the new skeletal model to obtain data of the new model of muscles, tendons, and ligamenta for virtual links and the origins, end points, and via-points of muscles, tendons, and ligamenta in the coordinate system of the new skeletal model to generate the new-body-model data.

According to the eleventh solving means of the present invention there is provided, a computer-readable recording medium having stored thereon a new-body-model data generated by mapping, according to a standard body model which expresses a skeletal model and a model of muscles, tendons, and ligamenta of a standard body, the model of muscles, tendons, and ligamenta onto a new skeletal model which expresses a new body, the new-body-model data having a standard-skeletal-model data structure for rigid links expressing the geometric shape of a skeleton, and a new-model data structure for muscles, tendons, and ligamenta, when the muscles, tendons, and ligamenta are expressed by wires, for the origins, end points, and via-points, or for the origins and end points of the wires, and defining a new body model, the standard-body-model data defining the standard body model by a standard-skeletal-model data for rigid links expressing the geometric shape of a skeleton, and a standard-model data structure for muscles, tendons, and ligamenta, when the muscles, tendons, and ligamenta are expressed by wires, for the origins, end points, and via-points, or for the origins and end points of the wires, and the processing section (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the positions of the origins, end points, and via-points, or the origins and end points of the wires in the standard skeletal model onto the new skeletal model to obtain data of the new model of muscles, tendons, and ligamenta for the origins, end points, and via-points, or the origins and end points of muscles, tendons, and ligamenta in the coordinate system of the new skeletal model to generate the new-body-model data.

BRIEF DESCRIPTION OF THE DRAWINGS

FIG. 10 is a view showing a format of a Transform node.

FIG. 11 is a view showing a hierarchical structure of VRML data which includes information of muscles, tendons, and ligamenta and bone-shape data.

BEST MODE FOR CARRYING OUT THE INVENTION

A. Body Dynamics Calculation Method and Body Dynamics Model

1. Dynamics Model 1-1. Overview

Figure 1:
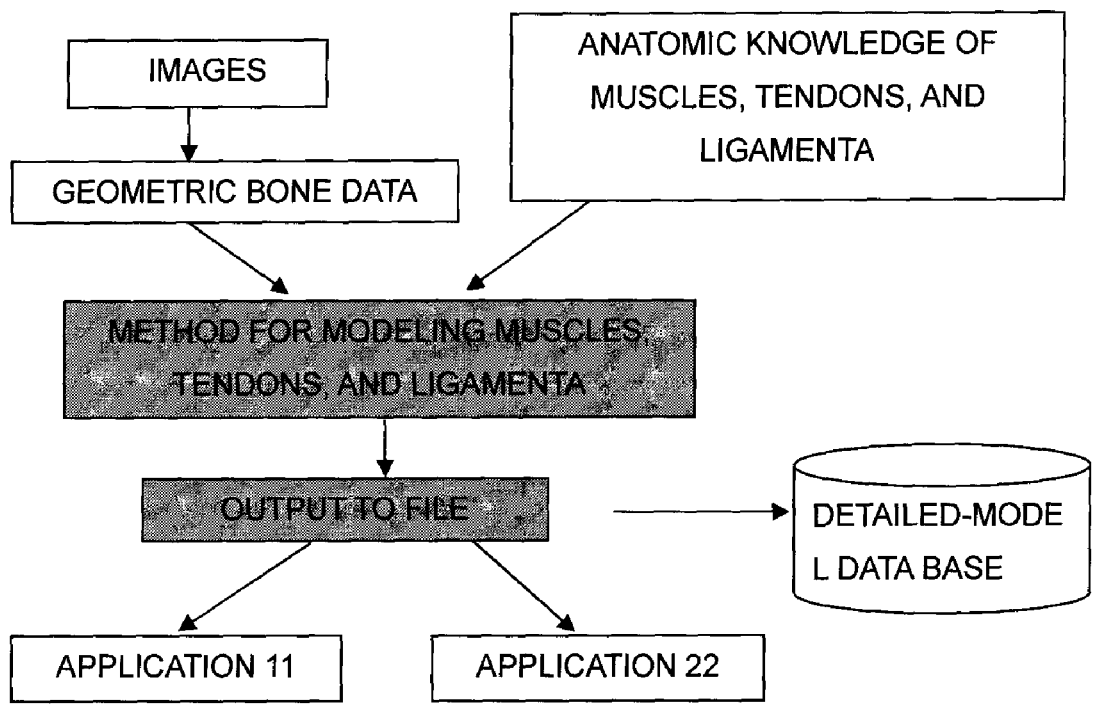
FIG. 1 is a view showing a system which uses the present embodiment.

FIG. 1 is a view showing a system which uses the present embodiment. In the system, a geometric bone model is obtained from images of bones generated in medical units such as an MRI and a CT, and a model of muscles, tendons, and ligamenta is obtained from an anatomic knowledge for muscles, tendons, and ligamenta and the geometric bone model according to the present embodiment. When the model of muscles, tendons, and ligamenta is output in a format based on the present embodiment, the model can be used in analysis in various applications, and can also be input to a data base which has a great number of models. In the following embodiments, human-body models will be mainly described, but the present invention can be applied not only to human-body models but also to models of bodies, such as animal bodies and living bodies.

The present embodiment mainly includes the following two features.

Method for modeling muscles, tendons, and ligamenta with the use of wires/virtual links In this method, muscles, tendons, and ligamenta in a human body are modeled in wires each of which connects the origin and the end point fixed to a bone and which passes through no or one or more via-points fixed to a bone or a virtual bone.

Method for describing the above-described model in a VRML (virtual reality modeling language) format Information of muscles, tendons, and ligamenta is described in the VRML format, which is a standard description format for three-dimensional models, together with the three-dimensional geometric shape of a skeleton to allow the above-described model to be shared by various types of software.

Each of the two features will be described below in detail.

1-2. Method for Modeling Muscles, Tendons, and Ligamenta with the Use of Wires/Virtual Links Muscles, tendons, and ligamenta are defined as follows:
Muscles: Connecting a bone to another bone, and changing the length relatively freely.
Tendons: Locating at both ends of a muscle to connect the muscle to a bone
Ligamenta: Connecting a bone to another bone, and changing the length little.

Figure 2:
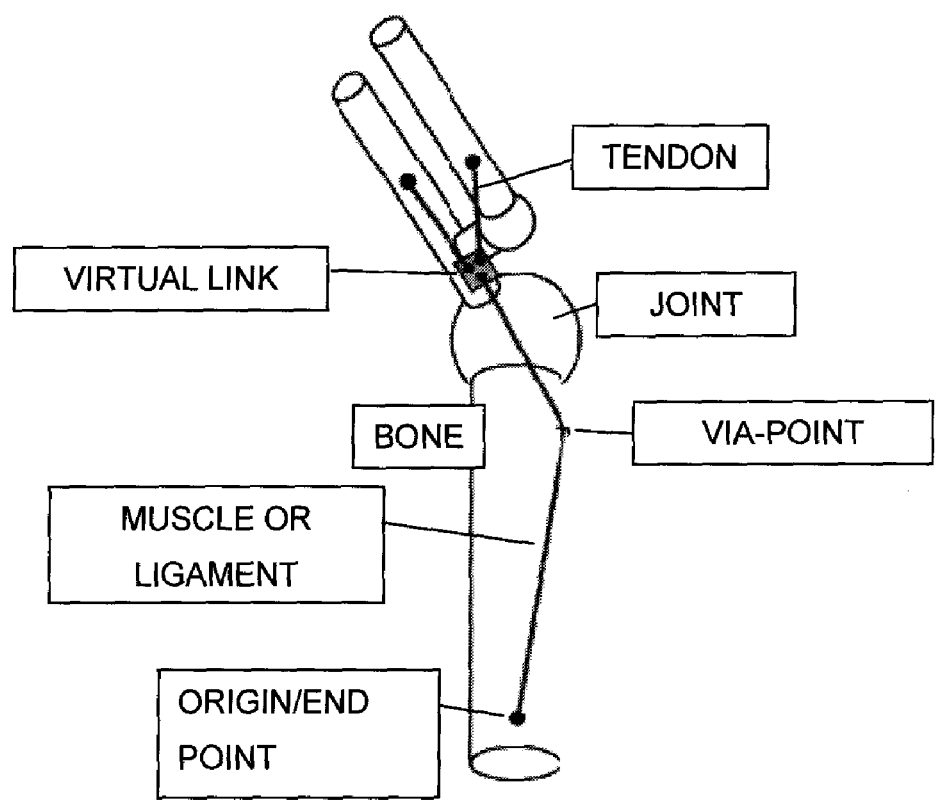
FIG. 2 is a view showing a wire model of muscles, tendons, and ligamenta.

FIG. 2 is a view showing a wire model of muscles, tendons, and ligamenta. Muscles, tendons, and ligamenta are modeled in wires each of which connects the origin and the end point fixed to a bone or a virtual bone (virtual link) and which passes through no or one or more via-points. The following principle is used to generate a model from anatomic information (some actual cases will be described later).

A virtual link is introduced when a muscle or a ligament branches at an end.

A via-point is introduced when a wire passes through a fixed point such as a protrusion of a bone and the wire can slide freely before and after or around the point.

When an end of a muscle is connected to one bone or to a virtual link, tendons at both ends of the muscle are not included in the model. A tendon is introduced only when an end of a muscle branches off in two or more directions.

The following steps are used to generate a model.
(a) Designing the connections, the arrangement, and the number of wires/virtual links used in the model Determine the arrangement and the connections of the wires and the virtual links by referring to an anatomy textbook or others.
(b) Positioning the virtual links, and the origin, a via-point, and the end point of each wire
Input the three-dimensional positions of the virtual links and each point by using a commercially available modeling software.
(c) Storage of information of a skeleton and muscles, tendons, and ligamenta Add names and hierarchical structures to the wires, the virtual links, the origins, the end points, and the via-points according to a rule described later, and output them in the VRML format together with the geometric information of the skeleton.

An example of step (a) will be described next by the following order.
(1) Model in which one part is replaced with one simple wire formed of only an origin and an end point
(2) Model in which one part is replaced with one wire formed of an origin, a via-point, and an end point
(3) Model in which one part is replaced with a plurality of wires
(4) Model in which one part is replaced with a virtual link and a plurality of wires
(5) Compound model Each of the above-described models will be described below.

Figure 3:
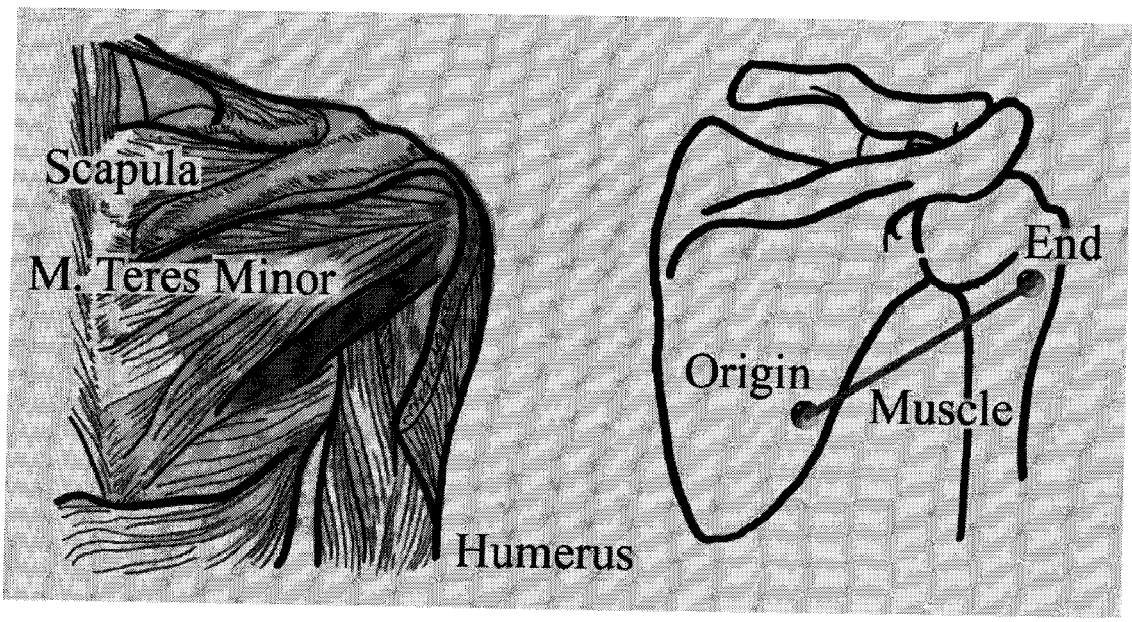
FIG. 3 is a view of a model of an m. teres minor, which ends at a humerus.

(1) Model in which One Part is Replaced with One Simple Wire Formed of Only an Origin and an End Point FIG. 3 is a view of a model of an m. teres minor, which ends at a humerus.

Many muscles and tendons each are modeled in one simple wire formed of only both edge points, an origin and an end point.

Figure 4:
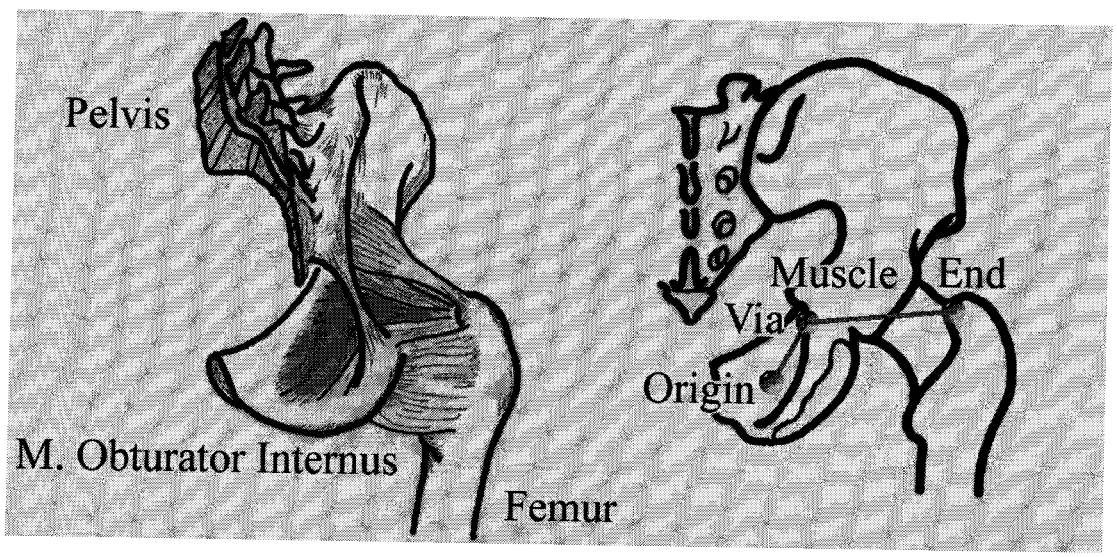
FIG. 4 is a view of a model of an m. obturator internus located at the stomach side of the pelvic girdle.

(2) Model in which One Part is Replaced with One Wire Formed of an Origin, a Via-Point, and an End Point FIG. 4 is a view of a model of an m. obturator internus located at the stomach side of the pelvic girdle.

In this case, a lesser sciatic notch where a muscle runs serves as the fulcrum of muscle action. In such a case, the muscle tension is not on the straight line connecting the origin and the end point. Therefore, a via-point is inserted in order to show a correct muscular-tension direction in the model. A via-point is inserted not only when a muscle is caught by a part of a bone, such as the case of an m. obturator internus, but also when the tendon restraint caused by a tendon sheath is modeled.

(3) Model in which One Part is Replaced with a Plurality of Wires

Figure 5:
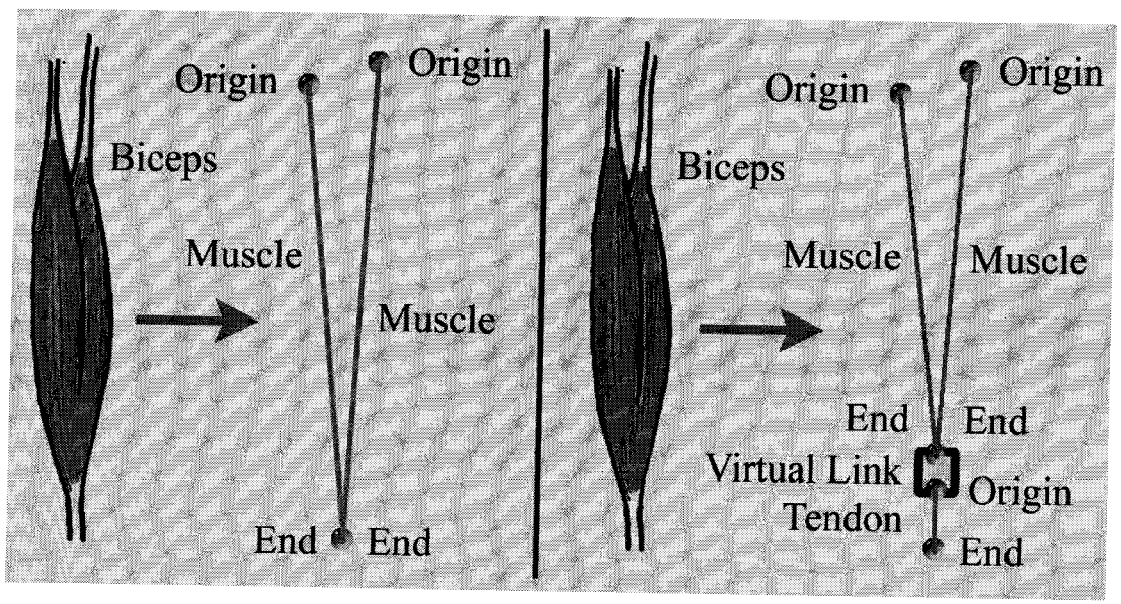
FIG. 5 is a view of a model of an m. pectoralis major.

FIG. 5 is a view of a model of an m. pectoralis major.

The functions of some muscles such as n-headed muscles having a plurality of origins and ending at one common tendon and splenius muscle having broad plate-shaped tendons, among various types of muscles, are modeled with the use of not one wire but a plurality of wires. N-headed muscles are modeled in n wires. Muscles having broad plate-shaped tendons are modeled in about two to four wires when the muscles are widely attached on a single bone, and modeled in further more wires when the muscles are further widely attached to a plurality of bones.

Figure 6:
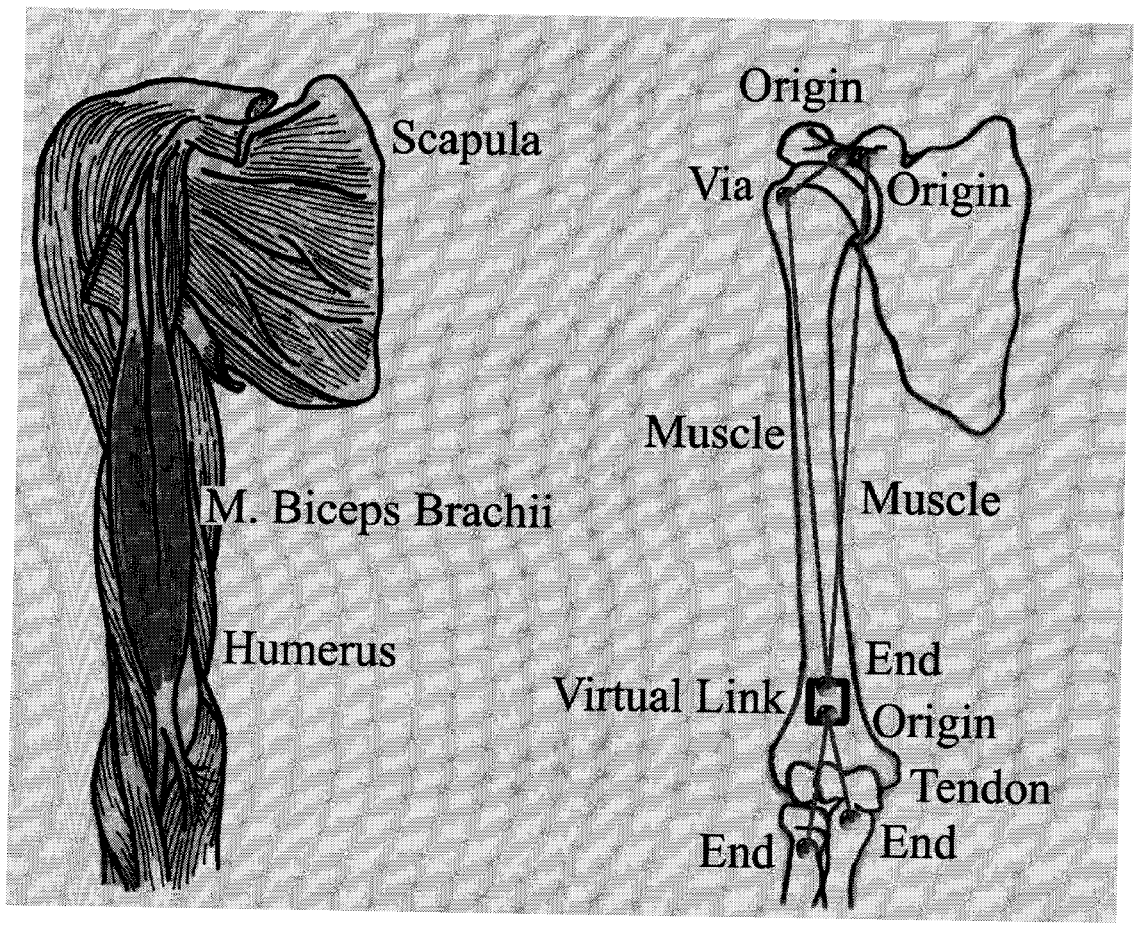
FIG. 6 is a view showing two models of a biceps.

(4) Model in which One Part is Replaced with a Virtual Link and a Plurality of Wires FIG. 6 is a view showing two models of a biceps. When the above-described modeling method (3) is applied to parts which include branches, such as n-headed muscles, many branch points serve as the end points of muscles (as shown in an upper section of FIG. 6). If the above-described modeling method (3) is insufficient, another method, (4), can be used in which a virtual link is introduced to provide a branch in a wire (as shown in a lower section of FIG. 6).

As a part which requires such a model, an m. biceps brachii can be taken.

Figure 7:
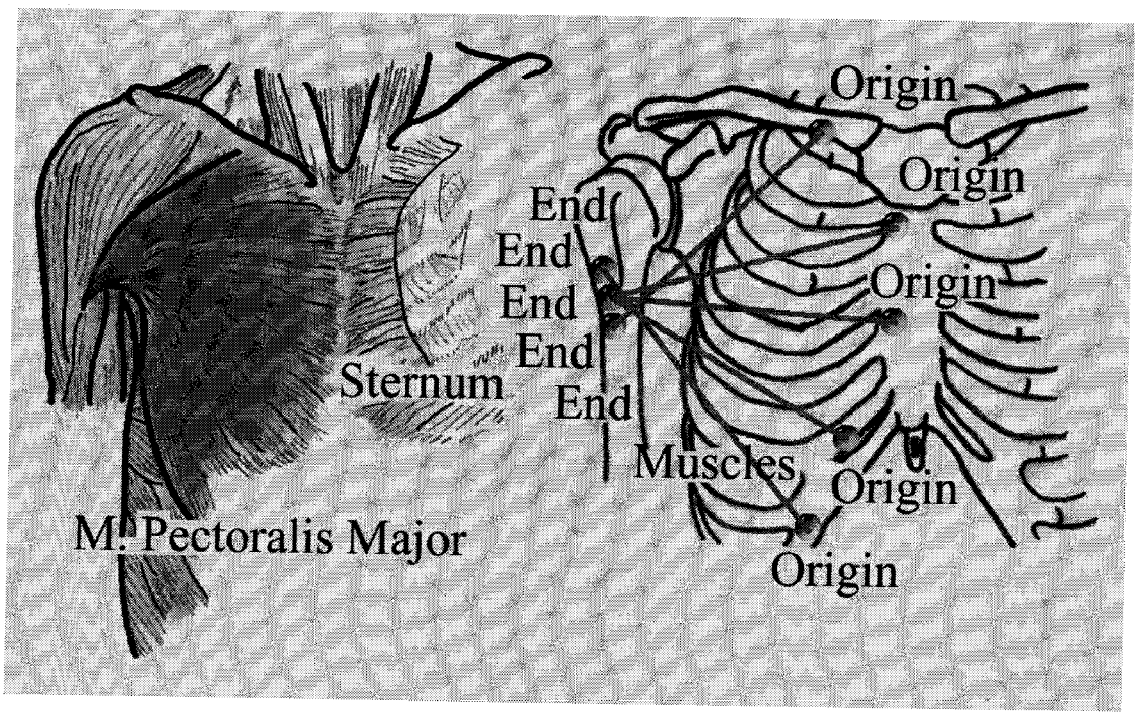
FIG. 7 is a view showing a model of an m. biceps brachii.

FIG. 7 is a view showing a model of an m. biceps brachii.

At an end section of the m. biceps brachii, branched tendons adhere to different bones. Therefore, to regenerate the function of the m. biceps brachii, the branched tendons need to be modeled. In this case, the m. biceps brachii is divided into two muscles (long-headed and short-headed) and two tendons, and a virtual link is located at the branch point of these muscles and tendons. The reason why a virtual link is needed to model a branch is that the wire model has the principle that a wire starts at one origin, passes through no or one or more via-points, and ends at one end point. This principle comes from a wire-tension calculation method. A virtual link can have no mass unlike a bone link, but can be treated as a link in that a relative position between points disposed on a virtual link is not changed, and tension is propagated. A virtual link can have a predetermined mass.

(5) Compound Model

A ligament disposed in an elbow joint will be taken as an example.

Figure 8:
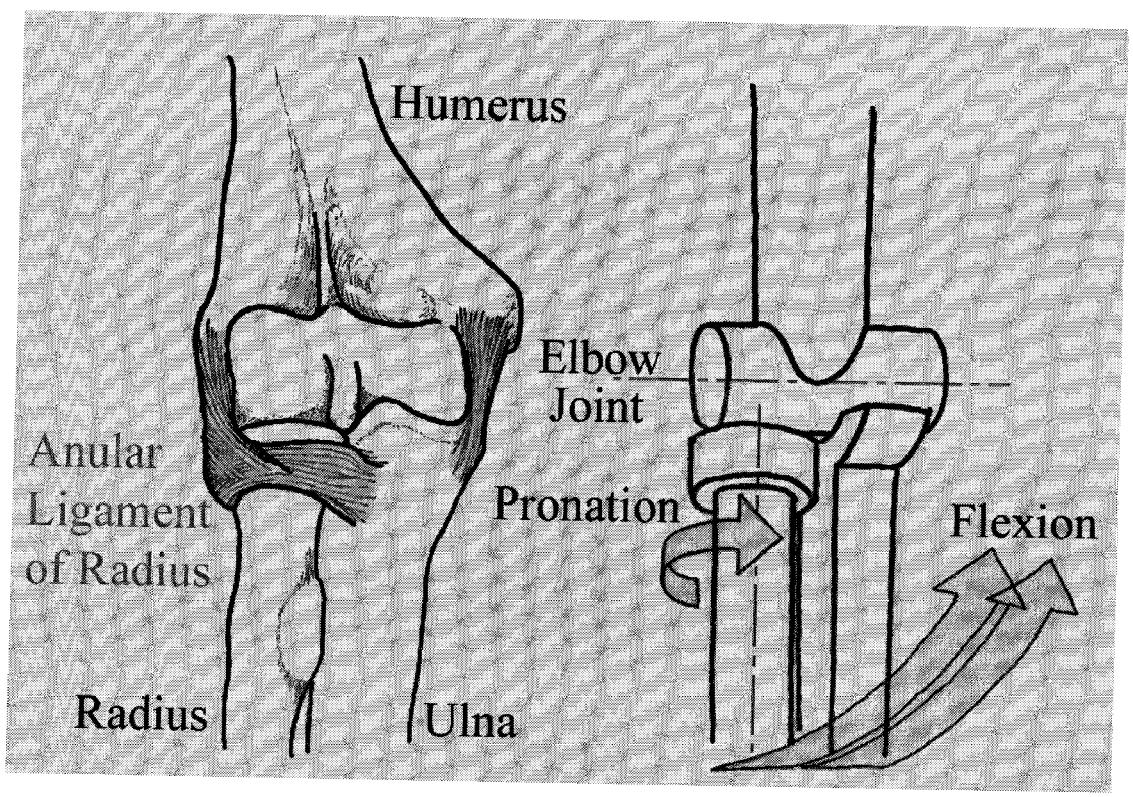
FIG. 8 is a view showing the arrangement of a ligament in an elbow joint and a pair given by the restraint of the ligament in the elbow joint.

FIG. 8 is a view showing the arrangement of a ligament in an elbow joint and a pair given by the restraint of the ligament in the elbow joint.

The restraint caused by the ligamenta at the left-hand side of FIG. 8 determines a pair in the joint as shown at the right-hand side of FIG. 8. A radius can pronate independently of an ulna, but they do not always move independently, and they tune with each other and rotate at flexion (and extension) between a brachium and an forearm. To model such a complicated ligament arrangement, a compound model in which a simple-wire model having via-points and a plural-wire model having virtual links are combined is used.

Figure 9:
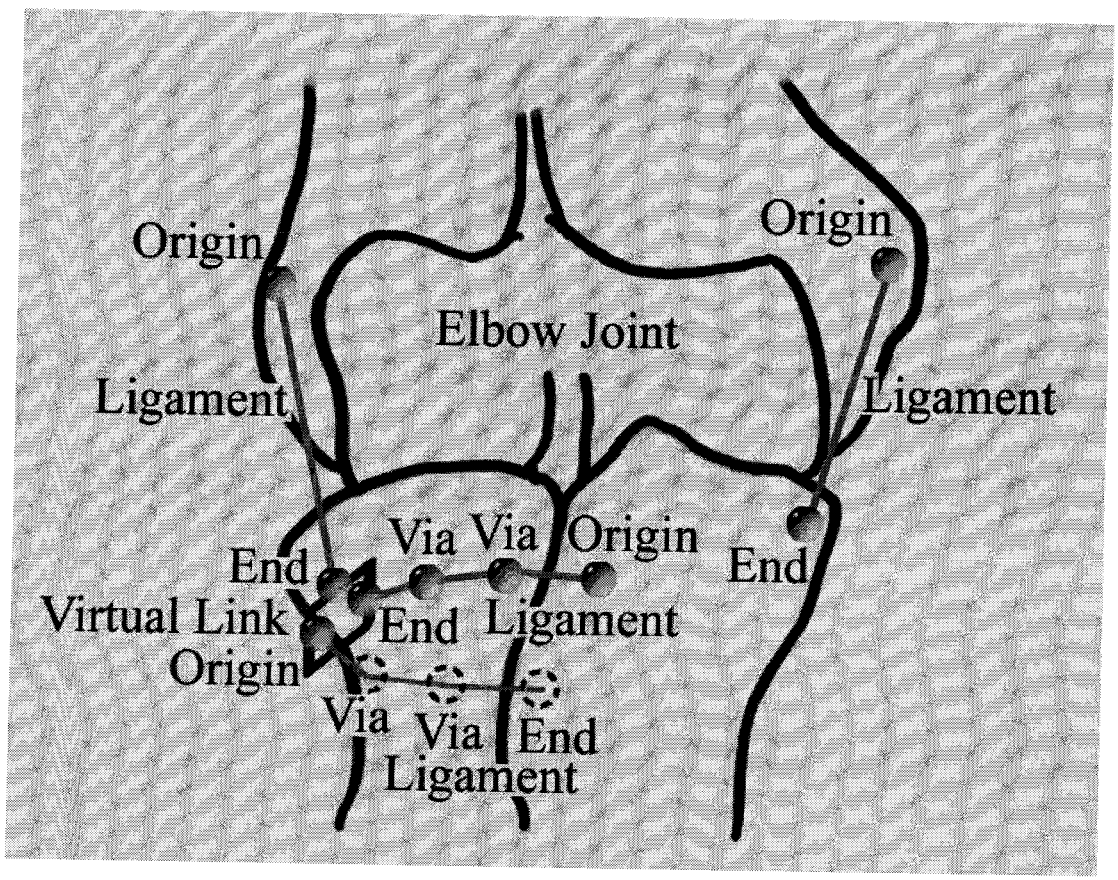
FIG. 9 is a view showing a model of the ligament in the elbow joint.

FIG. 9 is a view showing a model of a ligament in an elbow joint.

A pair of a radius and an ulna is modeled by a semilooped ligament which starts at the ulna, holds the radius with via-points, and ends at the ulna. To model a ligament disposed between a brachial bone and an antebrachial bone, a virtual link is placed on the semilooped ligament, and then three ligamenta attached to the virtual link are placed in a T shape. A cartilage can also be modeled in this way.

1-3. Method for Describing the Above-described Models in the VRML Format

It is necessary to describe the above models in a united format so that they can be used in various types of software and data bases. If a unique format is used, much labor is required to determine the specifications of the format. In addition, the development of software for reading is also a burden. In the present embodiment, it is taken into consideration that data includes not only numerical data of muscles, tendons, and ligamenta but also geometric data of bone shapes, and information of muscles, tendons, and ligamenta is described in the VRML (virtual reality modeling language) format, which is a standard format for describing shapes, texture, animation data, and others in virtual reality, and data specifications therefor were developed. Since many three-dimensional modeling software packages support reading and outputting of VRML files, the present invention allows the above-described models to be generated without using special software.

FIG. 10 is a view showing a format of a Transform node. In VRML, nodes are described with shapes and materials depending on the types of objects to be placed. Placing nodes in a hierarchical structure can define a range in which a node affects. In the present invention, to describe information of muscles, tendons, and ligamenta, a Transform node for defining a coordinate conversion and a DEF node for assigning a unique name to a node are used. A typical format in a VRML file is shown in the figure. With this format, a Transform node called node_name is defined, and its position and posture can be specified by "translation" and "rotation", respectively.

Each of muscles, tendons, ligamenta, virtual links, origins, end points, and via-points is expressed by one Transform node. Transform nodes expressing origins, end points, and via-points serve as child nodes of Transform nodes expressing muscles, tendons, and ligamenta to which the origins, end points, and via-points belong. Transform nodes expressing muscles, tendons, ligamenta, and virtual links serve as child links of Transform nodes called muscles, tendons, ligamenta, and virtual_bones depending on their types. A group of nodes expressing bone shapes are also collected under a Transform node called bones.

The names of Transform nodes expressing muscles, tendons, ligamenta, and their origins, end points, and via-points are assigned according to the following naming rule. Any names can be assigned to virtual links.

Ligamenta: {R|L|C}_Lig_LigamentaName
Muscles: {R|L|C}_Mus_MuscleName
Tendons: {R|L|C}_Ten_TendonName
Origins: ElementName_Org_LinkName
End points: ElementName_End_LinkName
Via-points: ElementName_n_LinkName where R, L, and C indicate the right side of the body, the left side of the body, and the trunk of the body, respectively.

LigamentaName, MuscleName, and TendonName indicate the unique name of a ligament, a muscle, and a tendon, respectively.

ElementName indicates the name of the ligament, muscle, or tendon to which a via-point belong.

"n" indicates the number of a via point.

LinkName indicates the name of a bone or a virtual link where a via-point is secured.

EXAMPLE

Muscle name: L_Mus_Supraspinatus (suprasinatus at the left side of the body)

Point name: L_Mus_Supraspinatus_Org_lscapula (origin of a wire, secured to bone lscapula)

FIG. 11 is a view showing a hierarchical structure of VRML data which includes information of muscles, tendons, and ligamenta and bone-shape data.

In addition to these data items, bone polygon data, the position data of via-points, and others are included in an actual VRML file.

2. Hardware

Figure 12:
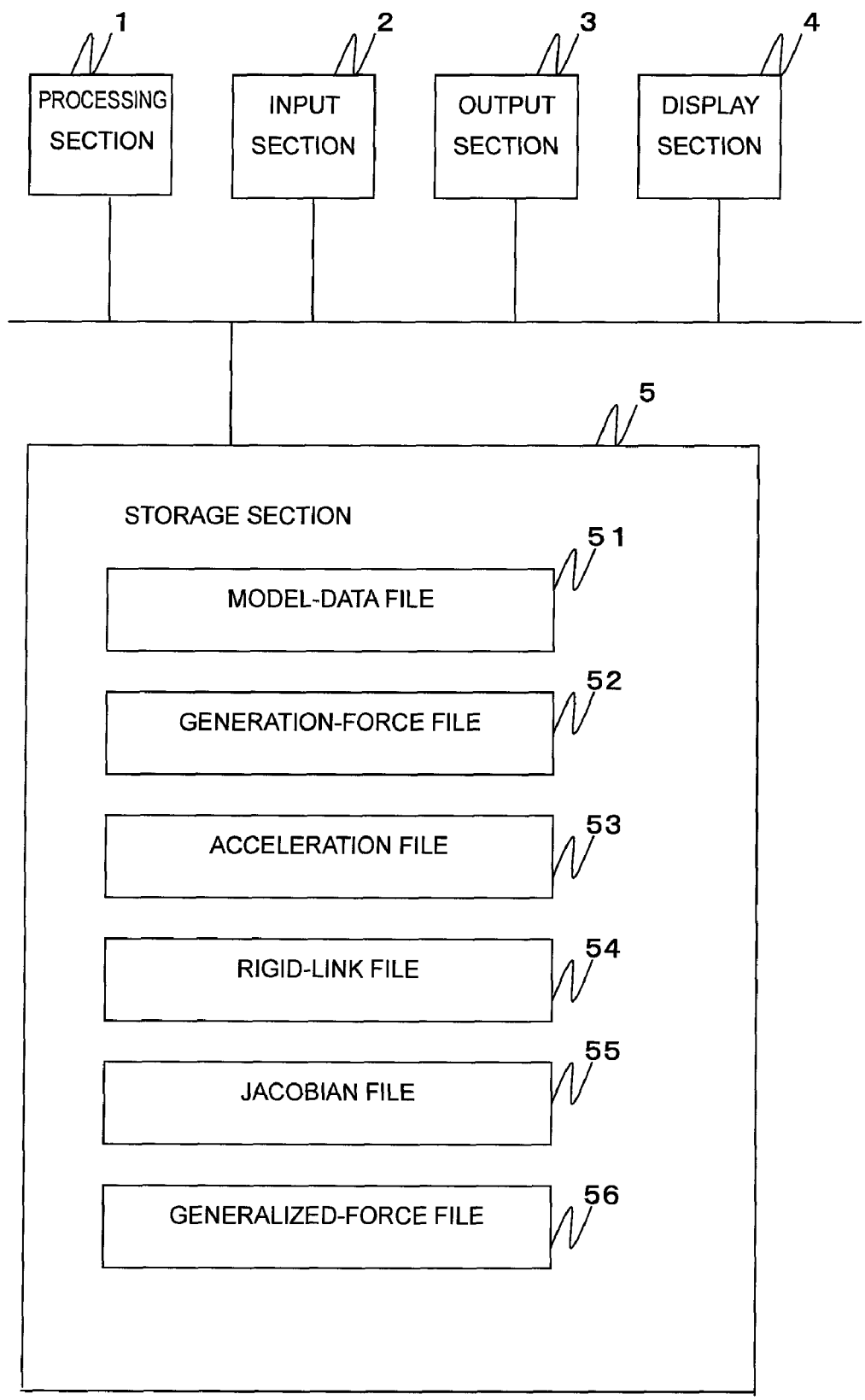
FIG. 12 is a structural view of hardware according to the present embodiment.

FIG. 12 is a structural view of hardware according to the present embodiment.

The hardware includes a processing section 1, which is a central processing unit (CPU), an input section 2, an output section 3, a display section 4, and a storage section 5. The processing section 1, the input section 2, the output section 3, the display section 4, and the storage section 5 are connected to each other by appropriate connection means such as a star connection or a bus connection.

The storage section 5 includes a model-data file 51 which has stored model data (steady data); a generation-force file 52 which has stored generation forces (generated forces or applied forces) of actuators corresponding to the wires/virtual links of muscles, tendons, and ligamenta, such as forces (tension) applied to the actuators by external forces (for example, an external force caused by a floor, a wall, or others, and an external force caused by motion) applied to rigid links and other forces, or forces which the actuators should generate; an acceleration file 53 which has stored the acceleration file 53 which has stored the acceleration of the rigid links such as acceleration applied to the rigid links or acceleration to be generated at the rigid links; a rigid-link file 54 which has stored the angles, positions, and velocities of the rigid links; a Jacobian file 55 for storing a calculated Jacobian, described later; and a generalized-force file 56 which has stored generalized forces (torque (for example, a spherical surface, three degrees of freedom) at the hinges (joints) of the rigid links).

The rigid links express a skeleton, and the wires/virtual links express muscles, tendons, and ligamenta.

As model data, the following example data is shown.

Shape data of rigid links

Dynamics data such as the mass, the inertial moment, and the center of mass of each rigid link Positions of the edge points and via-points of wires Shape data of virtual links (which may be either rigid links having mass or rigid links having no mass)

Dynamics data of virtual links

3. Dynamics Calculation Method 3-1. Overview

Figure 13:
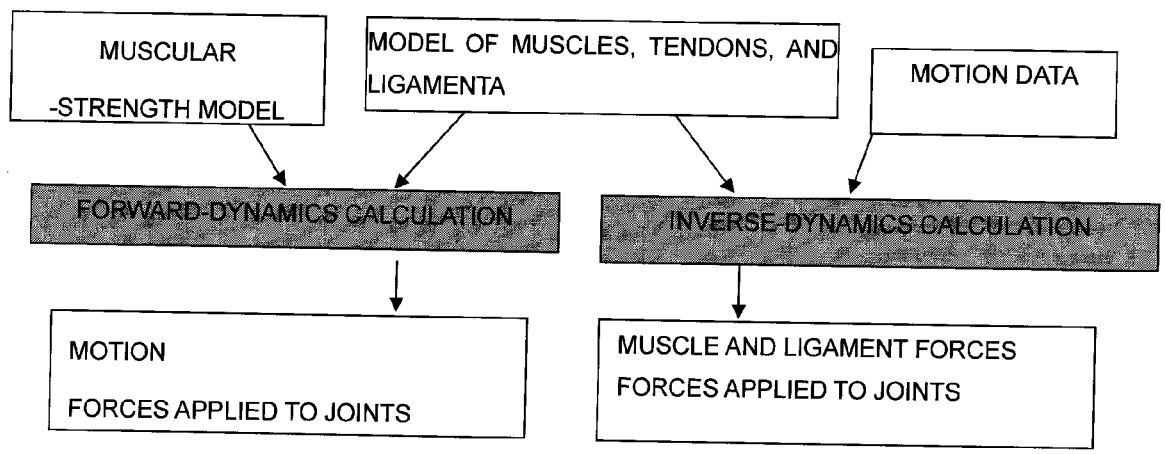
FIG. 13 is a view showing a system which uses the present embodiment.

FIG. 13 is an example view of a system which employs the present embodiment. With the use of the forward-dynamics calculation method according to the present embodiment, motion to be generated, forces to be applied to joints, and others can be calculated from a detailed model which includes muscles, tendons, and ligamenta, and a muscular-strength model. In the forward-dynamics calculation method, the muscular-strength model and the model of the muscles, tendons, and ligamenta are used as input data, and the motion and the forces to be applied to joints are used as output data. With the use of the inverse-dynamics calculation method, from the detailed model and motion data, forces generated by muscles and ligamenta to perform the motion, forces applied to joints at that time, and others can be calculated. In the inverse-dynamics calculation method, the motion data and the model of muscles, tendons, and ligamenta are used as input data, and the forces of the muscles, tendons, and ligamenta, and the forces applied to the joints are used as output data.

In the present embodiment, as the model which includes muscles, tendons, and ligamenta, the wire/virtual link model described in "1. Dynamics model" is especially used for the muscles, tendons, and ligamenta of a human body.

Figure 14:
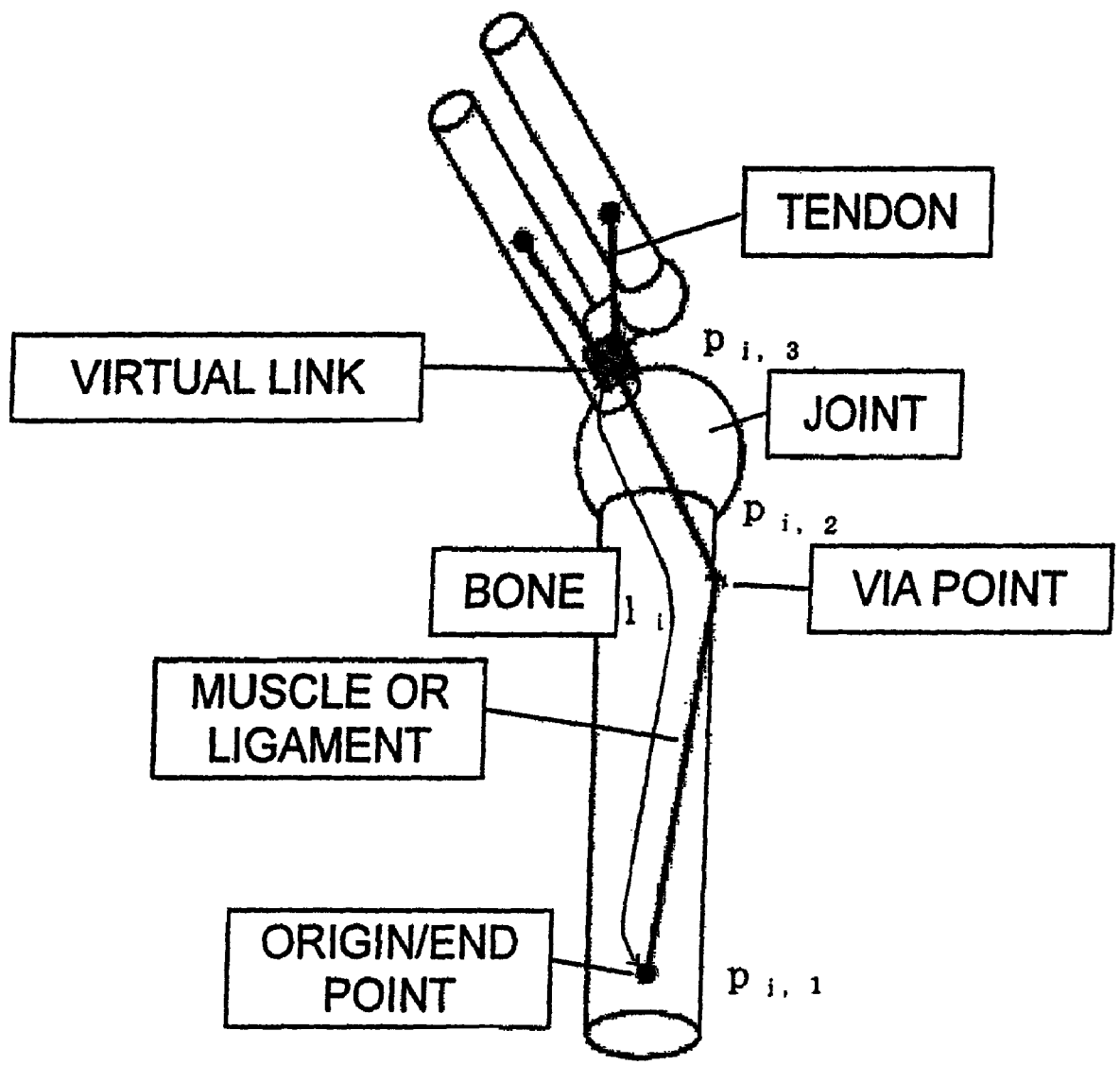
FIG. 14 is a structural view of a wire model of muscles, tendons, and ligamenta.

FIG. 14 shows the structural view of a wire model of muscles, tendons, and ligamenta. The dynamics calculation method will be described with such a dynamics model being used as an example. This calculation method can also be applied in the same way to the other models described in "1-2. Method for modeling muscles, tendons, and ligamenta by using wires/virtual links".

As shown in the figure, the model expresses one muscle or ligament as a wire connecting a origin and an end point through a via-point. A virtual link is a special link introduced to express a muscle or ligament having two or more edge points, and is a virtual bone having no mass and no inertial moment. In dynamics calculation, the resultant force operated on a virtual link should always be zero.

3-2. Preparations for Dynamics Calculation

As preparations for the forward-dynamics calculation and the inverse-dynamics calculation, Jacobians $J_{Li}$ for wire-length joint angles are obtained for all muscles, tendons, and ligamenta by calculations. $J_{Li}$ is a matrix which associates the time differential $l'_i$ of the length $l_i$ of a wire i with a generalized velocity $\theta'_G$ (joint angular velocity) as indicated by the following equation.

$$l'_i = J_{Li} \theta'_G$$

$J_{Li}$ is calculated according to the following procedure. Assuming that an element i is formed of $m_i$ edge points (which includes an origin and an end point) and via-points, $J_{Li}$ is expressed as the sum of $J_{Li,j}$, namely, $$J_{Li} = \sum_{j=0}^{m_i-1} J_{Li,j}$$

where $l_{i,j}$ indicates the distance between an end point or via-point j to an end point or via-point j+1, and $J_{Li,j}$ indicates the Jacobian for $\theta_G$ of $l_{i,j}$. Since $$l_{i,j}^2 = (p_{i,j+1} - p_{i,j})^T (p_{i,j+1} - p_{i,j})$$

where $p_{i,j}$ indicates the position of the via-point j, the following equation is obtained.

$$\begin{aligned} J_{Li,j} &= \frac{\partial l_{i,j}}{\partial \theta_G} \\ &= \frac{1}{l_{i,j}} (p_{i,j+1} - p_{i,j})^T \frac{\partial}{\partial \theta_G} (p_{i,j+1} - p_{i,j}) \\ &= \frac{1}{l_{i,j}} (p_{i,j+1} - p_{i,j})^T (J_{p_{i,j+1}} - J_{p_{i,j}}) \end{aligned}$$

Where $J_{p_{i,j}} = \partial p_{i,j} / \partial \theta_G$

Since $J_{p_{i,j}}$ is the Jacobian $p_{i,j}$ for $\theta_G$, it can be calculated by using methods such as that described in reference 4 shown below. $J_{Li}$ can be obtained by calculating the sum of $J_{Li,j}$ thus obtained.

(Reference 4)

D. E. Orin and W. W. Schrader, "Efficient Computation of the Jacobian for Robot Manipulators," International Journal of Robotics Research, Vol. 3, No. 4, pp. 66-75, 1984 (method for calculating at high speed Jacobians for joint angles at link positions)

With the use of the matrix $J_L$ ($J_L = [J_{L1} \, J_{L2} \ldots J_{Li} \ldots]$) which collects $J_{Li}$ for all wires, the relationship between a force f generated by a muscle or tendon and a generalized force $\tau_G$ equivalent thereto is expressed by the following equation.

$$\tau_G = J_L^T f \qquad (1)$$

According to this equation, procedures for the forward-dynamics calculation and the inverse-dynamics calculation will be described.

3-3. Forward-dynamics Calculation

Since muscular strength (generation force) f is given in the forward-dynamics calculation, $\tau_G$ is calculated by equation (1), and the calculation is performed according to a relevant invention, "Link-System Dynamics High-Speed Calculation Method (Japanese Patent Application No. 2001-228804)" or others.

Figure 15:
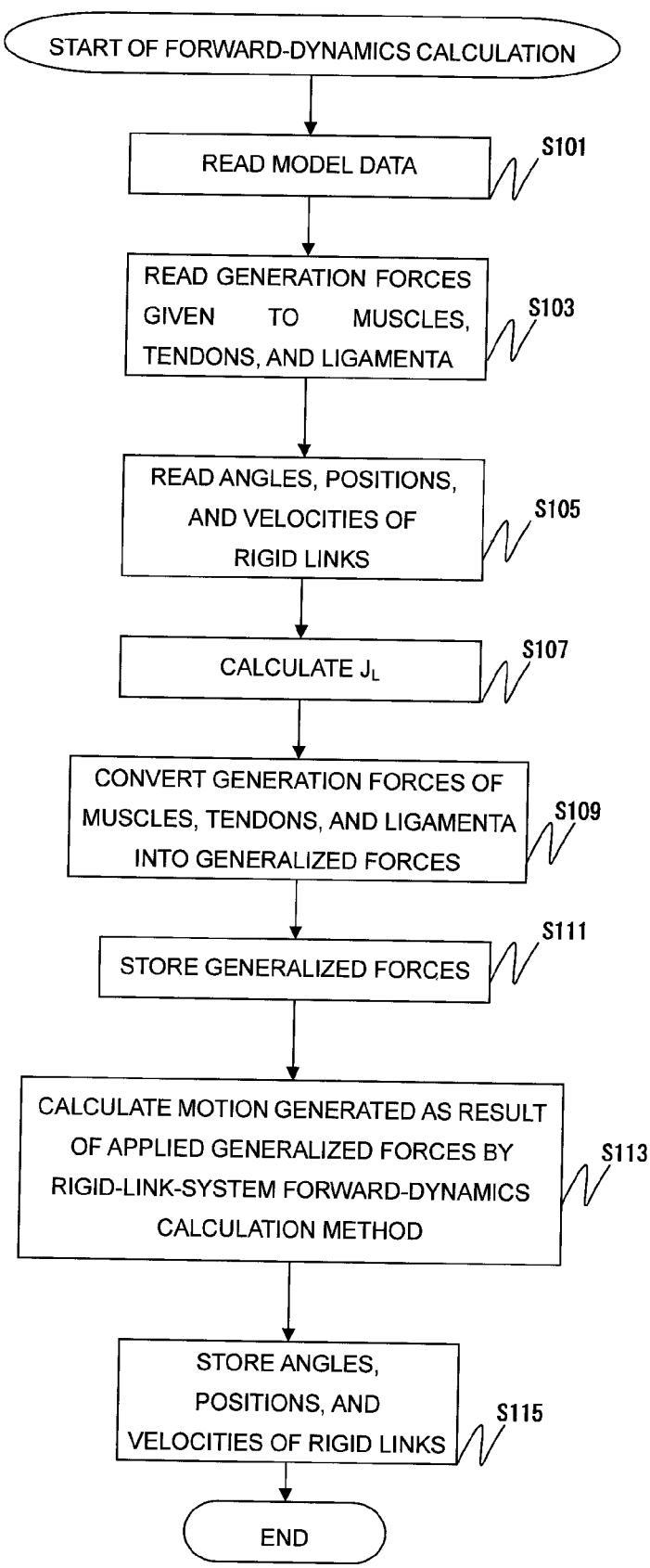
FIG. 15 is a flowchart of forward-dynamics calculation.

FIG. 15 is a flowchart of the forward-dynamics calculation.

The processing section reads model data which includes the shapes and the dynamics data of rigid links and wires/virtual links for which a dynamics calculation is to be performed, from the model-data file in the storage section (in step S101). The processing section reads from the generation-force file 32 in the storage section (in step S102) the generation force f generated at or applied to the wires/virtual links corresponding to the actuators of muscles, tendons, and ligamenta, such as external forces applied to rigid links or desired forces to be generated both of which are applied to a body model. The processing section reads the current angles, positions, and velocities of the rigid links from the rigid-link file 34 in the storage section (in step S103). The processing section calculates the Jacobian $J_L$ for the joint angle of a wire length according to the model data and the rigid-link data (in step S104).

Figure 16:
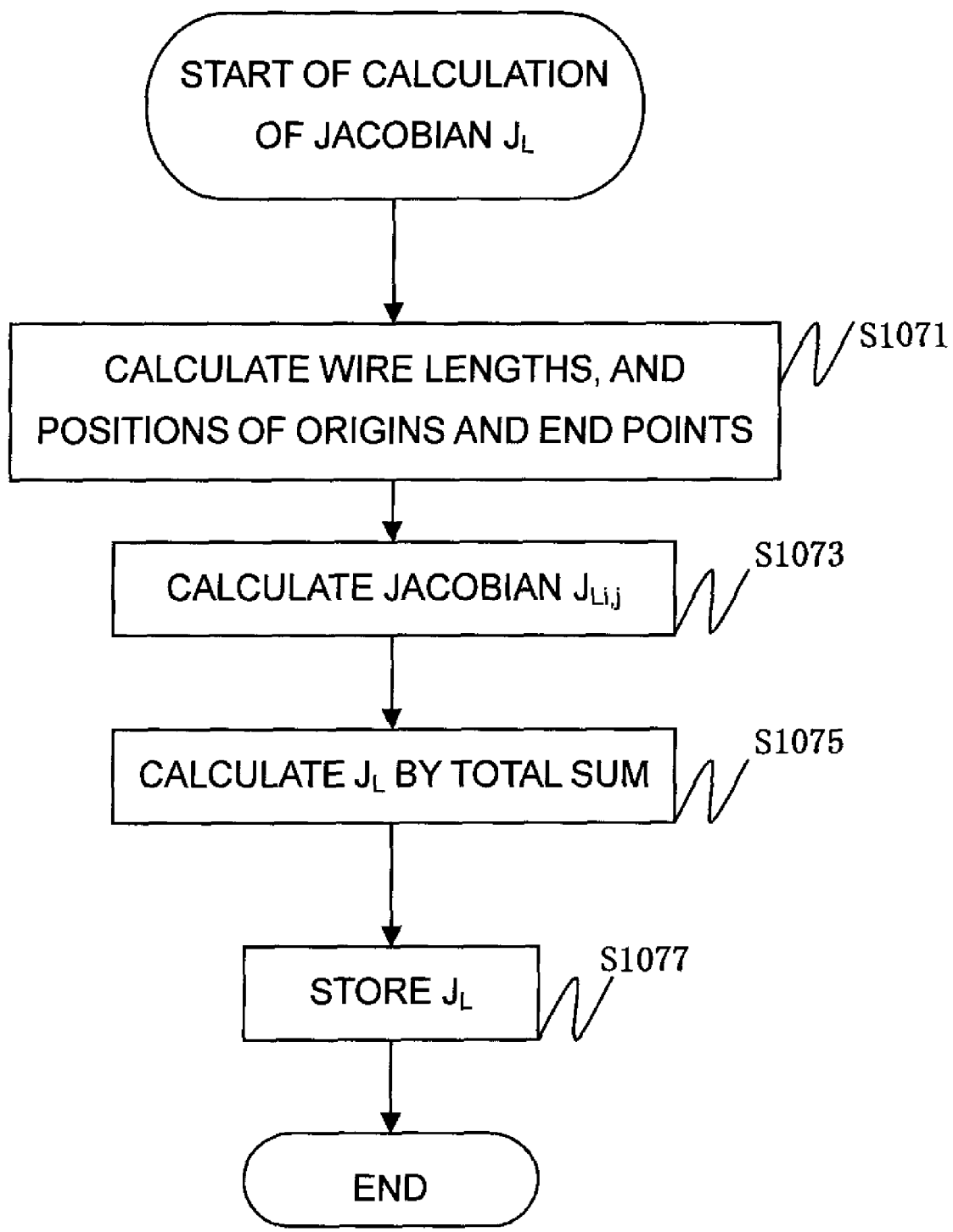
FIG. 16 is a flowchart of the calculation of a Jacobian $J_L$.

FIG. 16 is a flowchart of a Jacobian $J_L$ calculation. As described in "3-2. Preparations for dynamics calculation", $J_L$ can be obtained by the following procedure.

(1) The processing section calculates the wire length l and the positions $P_{i,j}$ of via-points (which include the origin and the end point) of a wire i from the model data and the current angles, positions, and velocities of the rigid links (in step S1071).
(2) The processing section calculates the Jacobian $J_{Li,j}$ according to equation 2 (in step S1073).
(3) The processing section calculates the sum of the obtained $J_{Li,j}$ according to equation 1 to obtain $J_{Li}$, and then obtains $J_L$ by calculating $J_L=[J_{L1}\ J_{L2}\ \ldots J_{Li} \ldots]$ (in step S1075).
(4) The processing section stores $J_L$ in the Jacobian file (in step S1077).

The processing section converts the read generation force f of the muscles, tendons, and ligamenta to a generalized force $\tau_G$ by using the obtained $J_L$ according to equation (1) (in step S105). In other words, the processing section converts the generation force f to the torque (for example, spherical surface, three degrees of freedom) at a hinge (joint) of the rigid link. The processing section stores the obtained generalized force $\tau_G$ in the generalized-force file 35 of the storage section (in step S107).

The processing section calculates the motion generated as a result of receiving the generalized force $\tau_G$ by a rigid-link-system forward-dynamics calculation method (in step S109). More specifically, the processing section obtains the acceleration of the rigid links in the whole body from the generalized force $\tau G$ and the current angles and positions of the rigid links, and calculates from the obtained acceleration the velocity and position obtained as a result of the motion of each rigid link. The processing section stores the angles, positions, and velocities of the rigid links in the rigid-link file 34 (in step S109). Data calculated at each state or at each timing can be stored, if necessary, corresponding to an identification number or others such as the time or the order.

The rigid-link-system forward-dynamics calculation method will be described below. It is assumed that the following equation is given.

$$\theta''=A^{-1}(\theta)\{\tau_G-B(\theta,\theta')-C(\theta)\}$$

where $\theta$ indicates the angle, $\theta'$ indicates the velocity, $\theta''$ indicates the acceleration, $A(\theta)$ indicates the inertial matrix, $B(\theta, \theta')$ indicates the Corioli's centrifugal force, and $C(\theta)$ indicates the gravity. $A(\theta)$, $B(\theta, \theta')$, and $C(\theta)$ are determined by the model data and others.

In the forward-dynamics calculation method, $\theta''$ (acceleration) is obtained according to the foregoing equation when $\tau_G$, $\theta$ (angle), and $\theta'$ (velocity) are given.

3-4. Link-system Dynamics High-speed Calculation Method
3-4-1. Overview

The calculation method is formed of the following procedure (see Japanese Patent Application No. 2001-228804).

Step 1. Assembling. Joints are added one by one at a state where all links are independent without any restraints caused by joints. The restraint force at the new joint and the acceleration of joints which have not yet been added are calculated according to a virtual-work principle (see reference 5). The restraint force or the acceleration calculated at this time does not indicate actual values in a link system.

Step 2. Disassembly. Joints are cut in the order reverse to that used in step 1 to determine the restraint force of the cut joint and the joint acceleration in the actual link system.

(Reference 5)
Y. Nakamura and M. Ghodoussi, "Dynamics Computation of Closed-Link Robot Mechanisms with Nonredundant and RedundantActuators," IEEE Transactions on Robotics and Automation, Vol. 5, No. 3, pp. 294-302, 1989.

3-4-2. Example Link System

Figure 17:
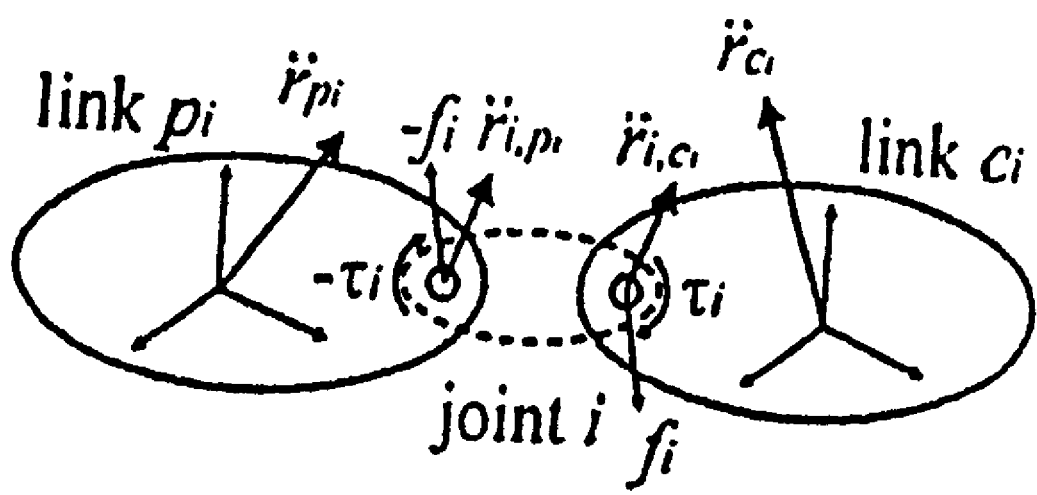
FIG. 17 is a view showing two links.

FIG. 17 is a view showing two links.

A specific calculation method will be described below with a two-link system formed of a joint i and rigid links $p_i$ and $c_i$ as shown in the figure being used as an example.

A kinematics relationship will be examined first. It is assumed here that $r'_{pi}$ and $r'_{ci}$ indicate the vectors which collectively include the parallel-movement velocities and angular velocities of coordinate systems secured to the links $p_i$ and $c_i$, where "'" indicates a differential, and the restraint condition of the joint i is indicated by the following equation.

$$K_{ci}(r'_{i,ci}-r'_{i,pi})=0 \quad (a1)$$

where $r'_{i,pi}$ and $r'_{i,ci}$ indicate the velocities of the centers of gravity of the links $p_i$ and $c_i$ at the position of the joint i, and a matrix $K_{ci}$ is calculated from model data (a joint angle, a rigid-link length, and others). It is also assumed in the same way that the joint velocity $\theta'_i$ of the joint i is expressed by the following equation.

$$\theta'_i=K_{Ji}(r'_{i,ci}-r'_{i,pi}) \quad (a2)$$

where a matrix $K_{Ji}$ is calculated by model data (the coupling point of links, and others). The relationships between $r'_{ci}$ and $r'_{i,ci}$, and $r'_{pi}$ and $r'_{i,pi}$ are expressed by the following equation with the use of Jacobians $J_{i,ci}$ and $J_{i,pi}$.

$$r'_{i,k}=J_{i,k}r'_k (k=c_i, p_i) \quad (a3)$$

The Jacobian $J_{i,k}$ is used to calculate the velocity of the center of gravity of the link from the velocity of the joint position.

The equation of motion will be next examined. The following equation of motion can be made.

$$M_{ci}r''_{ci}+C_{ci}=\tau_{Gci} (k=c_i, p_i) \quad (a4)$$

where $M_k$ indicates the inertial matrix of each link around the origin, $C_k$ indicates an item dependent on the gravity and velocity (the Corioli's centrifugal force of one link, the gyro effect), $\tau_k$ indicates a generalized force at the position of the center of gravity of the operating link, $k=c_i, p_i$, and $M_k$ and $C_k$ are calculated from the model data.

Assuming that $r_{pi}$ and $r_{ci}$ are generalized coordinates in this system, the two-link system can be regarded as a closed link mechanism where two link systems having six degrees of freedom are restrained by the joint i. The relationship among the restraint force $F_i$ (all forces generated at the joint other than torque), the joint torque $\tau_i$, and the generalized force are expressed as follows by the virtual-work principle (see the above-described reference).

$$\tau_{Gci}=H^T_{i,ci}F_i+H^T_{ji,ci}\tau_i \quad (a5)$$

$$\tau_{Gpi}=-H^T_{i,pi}F_i-H^T_{ji,pi}\tau_i \quad (a6)$$

where $H_{i,k}=K_{ci}J_{i,k}$, $H_{ji,k}=K_{Ji}J_{i,k}$, and $k=c_i, p_i$.

The restraint force Fi is obtained as follows by solving the equations obtained by time differentiating equations (a1) and (a3) and solving equations (a4) to (a6).

$$F_i=S^{-1}_{ii}(-S_{Jii}\tau_i+H_{i,ci}M^{-1}C_{ci}-H_{i,pi}M^{-1}_{pi}C_{pi})$$

$$S_{ii}=H_{i,pi}M^{-1}_{pi}H^T_{i,pi}+H_{i,ci}H^T_{i,ci}$$

$$S_{Jii}=H_{i,pi}M^{-1}_{pi}H^T_{Ji,pi}+H_{i,ci}M^{-1}_{ci}H^T_{Ji,ci}$$

With the use of these equations, the joint acceleration $\theta''_i$ is calculated.

The above-described calculation method can be expanded to find a calculation procedure for connecting any two link systems.

3-4-3. Parallel Calculation

The following calculation procedure is used for parallel calculation.

(1) All links are divided into the same number of groups as that of processes.
(2) Calculation for connecting links is performed in parallel in each group.
(3) Calculation for connecting groups obtained by step 2 is performed in parallel, if possible, to complete a link system.

The present calculation method has high parallelism in this way, and the optimum scheduling is possible according to the number of processes.

3-5. Inverse-dynamics Calculation

In inverse-dynamics calculation, $\tau_G$ is calculated first according to inverse-dynamics calculation for usual link systems by the use of a calculation method such as that shown in reference 6, described below, and then equation (1) is solved. At this time, it is necessary to make a model of muscles, tendons, and ligamenta in terms of their biomechanical characteristics according to the issues concerned. For example, since muscles, tendons, and ligamenta can generate only tensile force, a model having negative force components only can be assumed.

(Reference 6)
J. Y S. Luh, M. W. Walker, and R. P. C. Paul, "On-line Computational Scheme for Mechanical Manipulators," ASME Journal on Dynamic Systems, Measurement and Control, Vol. 104, pp. 69-76, 1980 (method for calculating link-system inverse dynamics at high speed).

Figure 18:
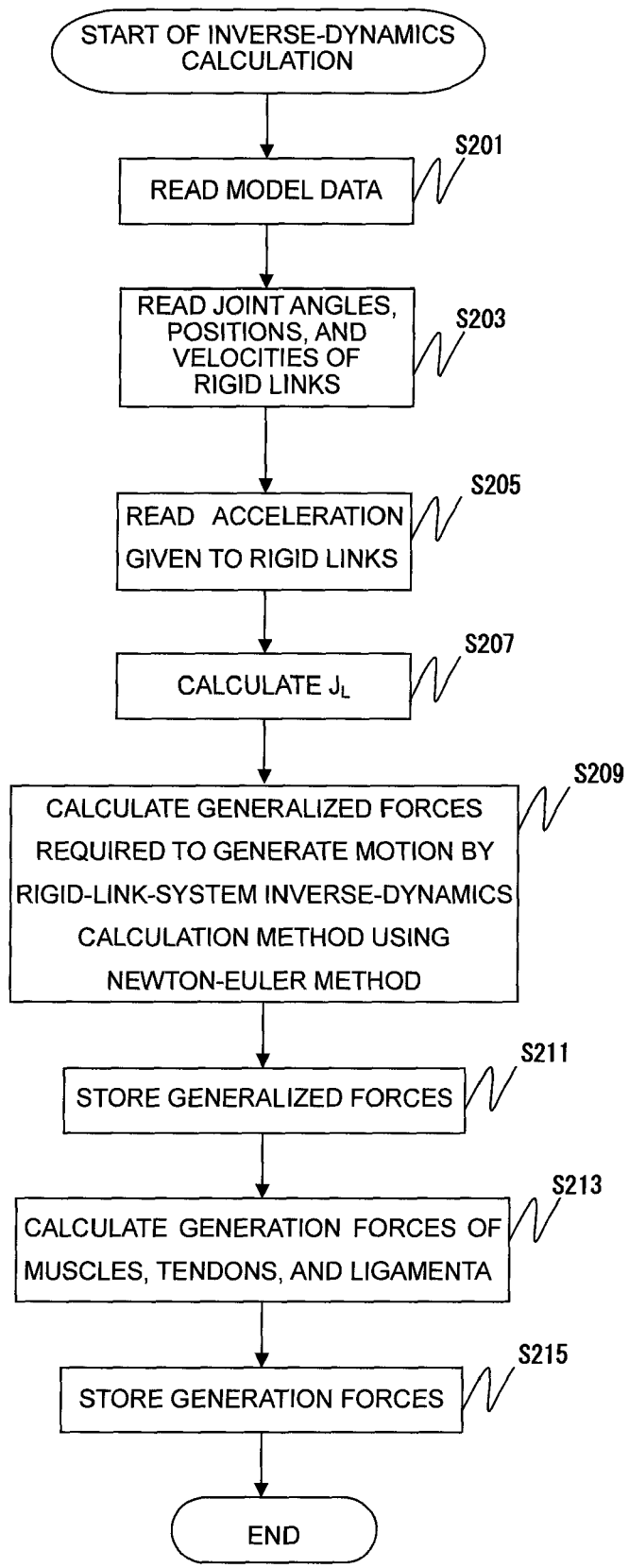
FIG. 18 is a flowchart of inverse-dynamics calculation.

FIG. 18 is a flowchart of the inverse-dynamics calculation.

The processing section reads model data which includes the shapes and the dynamics data of rigid links and wires/virtual links for which a dynamics calculation is to be performed, from the model-data file 31 in the storage section (in step S201). The processing section reads the current angles (joint angles), positions, and velocities of the rigid links from the rigid-link file 34 in the storage section (in step S203), and also reads acceleration given to the rigid links from the acceleration file 33 (in step S205).

The processing section calculates the Jacobian $J_L$ for the joint angle of each wire length, according to the model data and the current angles, positions, and velocities of the rigid links (in step S207), as described above.

With the use of a rigid-link-system inverse-dynamics calculation method such as the Newton-Euler method, the processing section calculates, according to the acceleration of the rigid links read from the acceleration file 33 and the angles and velocities read from the rigid-link file 32, generalized forces $\tau_G$ required to generate motion caused by the acceleration given to the rigid links (in step S209).

The rigid-link-system inverse-dynamics calculation will be supplementarily described below. It is assumed that the following equation is given.

$$A(\theta)\theta'' + B(\theta,\theta') + C(\theta) = \tau_G$$

where $\theta$ indicates the angle, $\theta'$ indicates the velocity, $\theta''$ indicates the acceleration, $A(\theta)$ indicates the inertial matrix, $B(\theta, \theta')$ indicates the Corioli's centrifugal force, and $C(\theta)$ indicates the gravity. $A(\theta)$, $B(\theta, \theta')$, and $C(\theta)$ are determined by the model data and others.

In the inverse-dynamics calculation method, $\tau_G$ is obtained according to the foregoing equation when $\theta$ (angle), $\theta'$ (velocity), and $\theta''$ (acceleration) are given.

The processing section stores the obtained generalized forces $\tau_G$ in the generalized-force file 35 of the storage section (in step S211).

The processing section calculates the generation force f generated at each wire/virtual link, corresponding to the tensile strength of the wires of muscles, tendons, and ligamenta which move the rigid links of the whole body, from the generalized forces $\tau_G$ with the use of the previously obtained $J_L$ according to equation (1) (in step S213). The processing section can also calculate the velocity and the acceleration of the rigid links obtained as a result of the motion, from the obtained generation forces. The processing section stores the obtained rigid-link generation forces f in the generation-force file 32 (in step S215).

B. Body-model Generation Method and Body Model

1. Overview of Body-Model Generation

Figure 19:
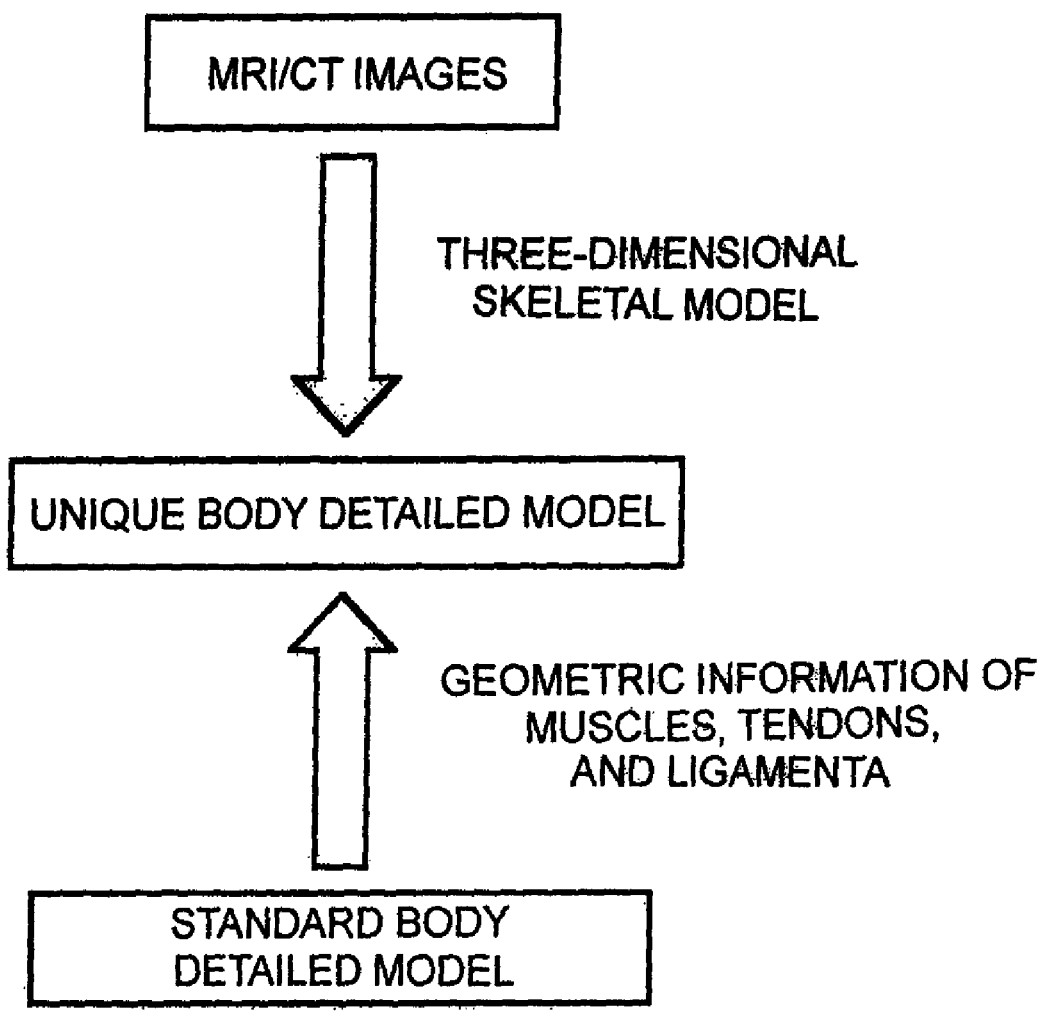
FIG. 19 is a view showing mapping outlines.

FIG. 19 is an outlined view of mapping of a model of muscles, tendons, and ligamenta in a body. This figure shows an example case in which geometric information of muscles, tendons, and ligamenta is mapped onto a three-dimensional skeletal model obtained from MRI/CT images, with the use of the present invention. A calculation engine according to the present invention compares a new skeletal model with the skeletal model of a standard body detailed model to calculate geometric information of muscles, tendons, and ligamenta in the new skeletal model to generate a unique body detailed model.

The standard body detailed model (standard body model) means a standard body model prepared in advance, and includes, for the body, skeletal-model data indicating a skeletal model and model data of muscles, tendons, and ligamenta, indicating the muscles, tendons, and ligamenta in the skeletal model.

The calculation engine (processing section) uses feature points arranged on the skeleton or automatically extracted, to calculate conversion parameters which match best a skeletal model from which a new body detailed model is to be generated, with the skeletal model of the standard body detailed model. The calculation engine further uses the calculated conversion parameters to map the geometric information of the muscles, tendons, and ligamenta in the standard body detailed model onto a new body model to generate the new human-body detailed model.

With the use of such a calculation engine, just by automatically extracting or manually giving several feature points to the standard body detailed model and the new skeletal model, the geometric information of the muscles, tendons, and ligamenta on the standard body detailed model can be mapped onto the new skeletal model. With this operation, work for generating a new body detailed model is considerably simplified in terms of labor compared with a case in which several hundreds of muscles, tendons, and ligamenta are manually added, and kinematics and dynamics analysis is made possible according to the body detailed data for an individual.

Figure 20:
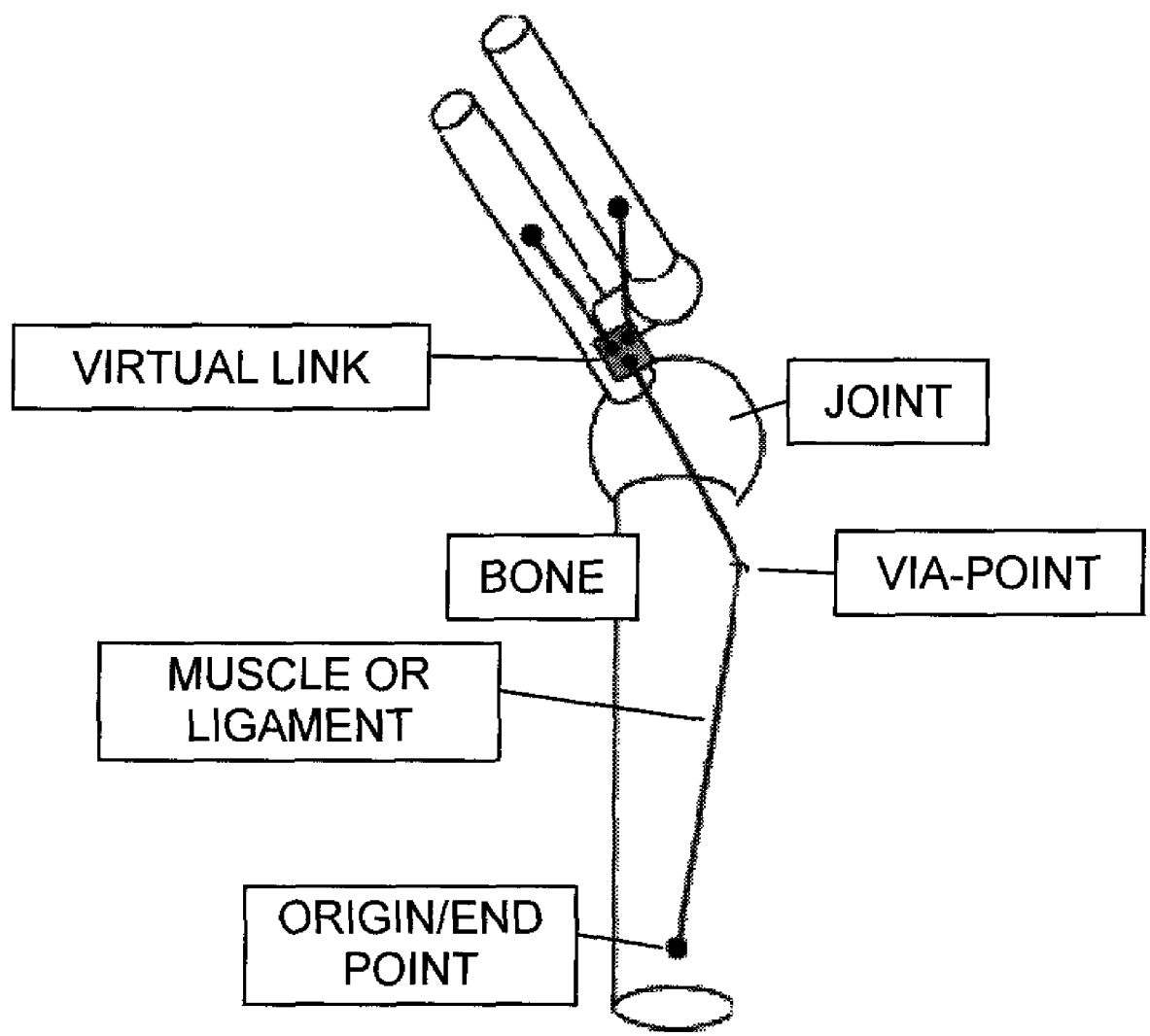
FIG. 20 is a view showing a model of muscles, tendons, and ligamenta by the use of wires/virtual links.

FIG. 20 is a view showing a model of muscles, tendons, and ligamenta, made by wires/virtual links. In the present invention, a dynamics model of muscles, tendons, and ligamenta in a human body such as that shown in the figure is used as a body detailed model. A human-body detailed model refers to a model in which data of muscles, tendons, and ligamenta is added to three-dimensional skeletal shape data. As models of muscle elements, tendon elements, ligament elements, and cartilage elements, wires having the origin and the end point secured to a bone and passing through zero or one or more via-points are generally used. As models of muscles and ligamenta having two or more edge points, virtual links are used.

The body detailed model prepared in advance is called a standard body detailed model (standard body model). The present invention provides a function for mapping the coordinate system and the geometric information of muscles, tendons, and ligamenta in the standard body model onto a new skeletal model (new skeletal model) of a new body detailed model (new body model) in which muscles, tendons, and ligamenta have not yet been defined, when the new body detailed model is generated. For example, corresponding points are obtained between different skeletons, the standard skeletal model of the standard body model and the new skeletal model of the new body model, and the coupling model of muscles, tendons, and ligamenta are mapped and converted from the standard skeletal model onto the new skeletal model.

2. Hardware.

Figure 21:
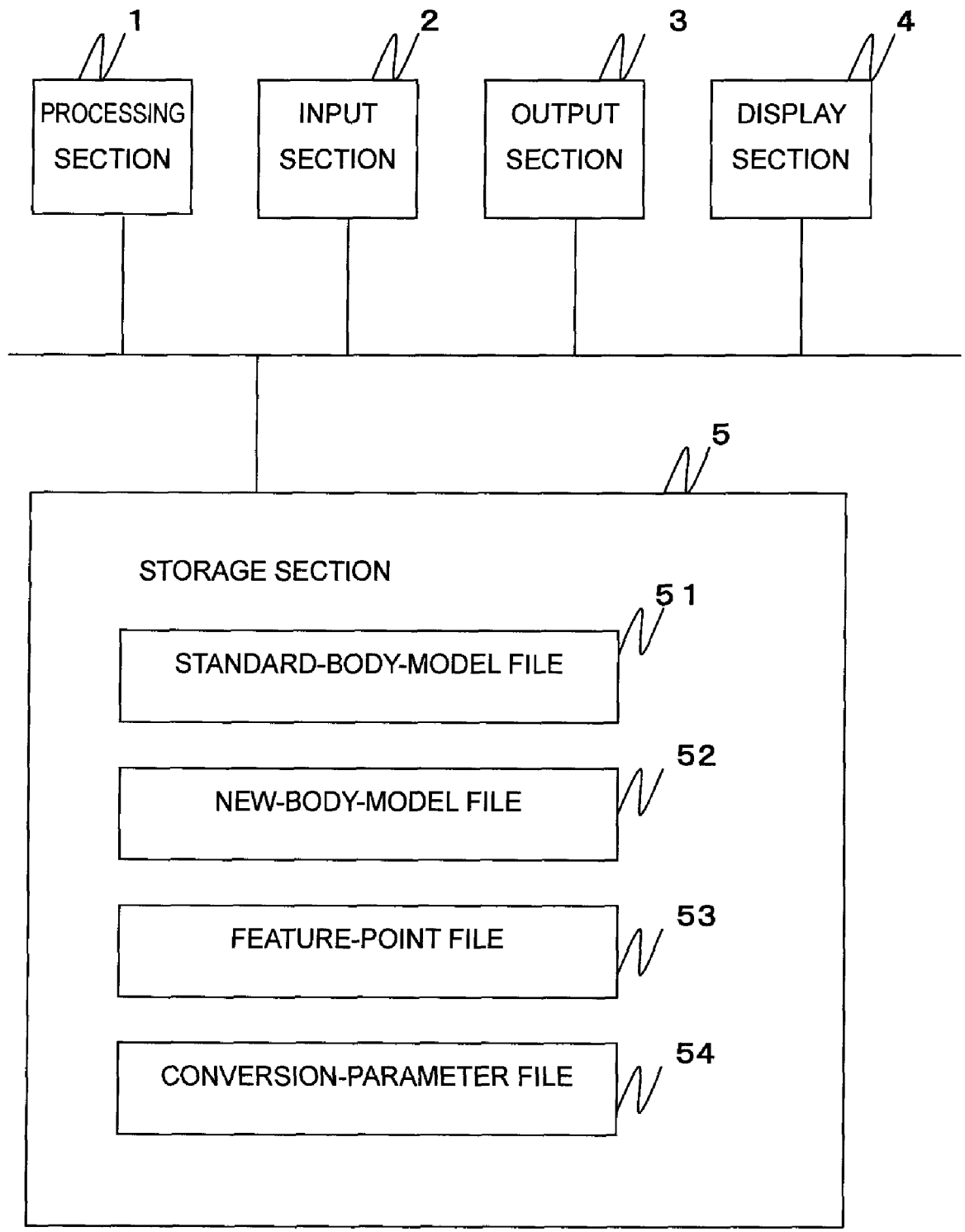
FIG. 21 is a structural view of a hardware according to the present embodiment.

FIG. 21 is a structural view of hardware according to the present embodiment.

The hardware includes a processing section 1, which is a central processing unit (CPU), an input section 2, an output section 3, a display section 4, and a storage section 5. The processing section 1, the input section 2, the output section 3, the display section 4, and the storage section 5 are connected to each other by appropriate connection means such as a star connection or a bus connection.

The storage section 5 includes a standard-body-model file 51, a new-body-model file 52, a feature-point file 53, and a conversion-parameter file 54. Rigid links express a skeleton, and wires/virtual links express muscles, tendons, and ligamenta.

The standard-body-model file 51 stores standard-model data for a standard body model which expresses a skeletal model and a model of muscles, tendons, and ligamenta of a standard body. The standard-body-model data defines the standard body model by standard-skeletal-model data for rigid links which express skeletal geometric shapes, and data of a standard model of muscles, tendons, and ligamenta for virtual links and the origins, end points, and via-points of wires, the wires and the virtual links connected between the wires being used to express the muscles, the tendons, and the ligamenta. The new-body-model file 52 stores new-body-model data defined by standard-skeletal-model data for rigid links which express skeletal geometric shapes, and data of a new model of muscles, tendons, and ligamenta for virtual links and the origins, end points, and via-points of wires, the wires and the virtual links connected between the wires being used to express the muscles, the tendons, and the ligamenta.

The feature-point file 53 associates feature points of each rigid link in the standard-skeletal-model data with corresponding feature points of the new-skeletal-model data defined by data for the rigid links of the new body model, and stores them. The conversion-parameter file 54 stores parameters for conversions which include parallel movement, rotational movement, and scaling, the parameters being used for mapping the data of the standard model of muscles, tendons, and ligamenta for the virtual links and the positions of the origins, end points, and via-points of the wires in the standard skeletal model onto the new skeletal model.

3. Body-model Generation Processing

Figure 22:
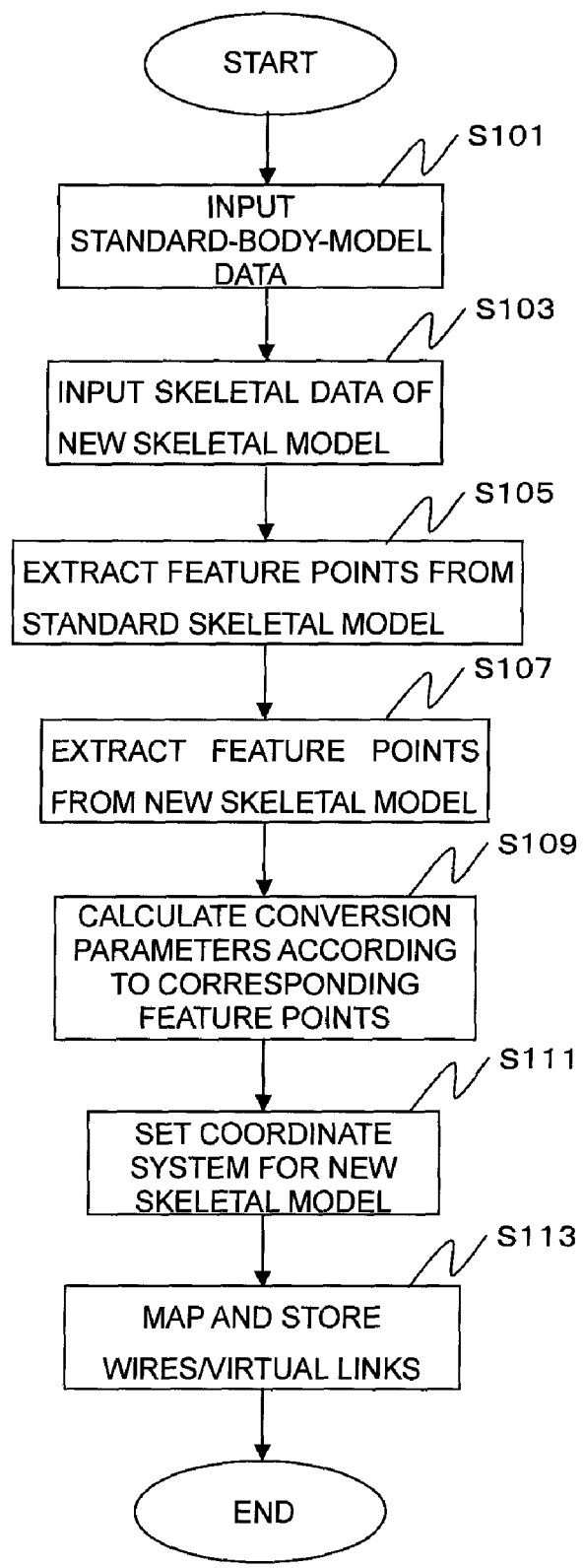
FIG. 22 is a view showing a flowchart of a body-model generation method.

FIG. 22 shows a flowchart of body-model generation processing.

The processing is broadly divided into the following two processes.

Setting a Coordinate System for the New Skeletal Model
In dynamics calculation, a limitation is imposed on the setting of coordinate systems in many cases. A coordinate system for the input new skeletal model is arranged so as to fit the coordinate system of the standard body detailed model.

Calculating and Setting the Positions of the Origins, End Points, and Via-Points of Wires The positions of the origins, end points, and via-points of the muscles, tendons, and ligamenta in the standard body detailed model are mapped onto the new skeletal model to complete the new detailed model.

A specific procedure will be described below.

The processing section inputs (in step S101) from the standard body file stored in the storage section, the standard-body-model data given in advance and defined by the standard-skeletal-model data for rigid links which express skeletal geometric shapes, and the data of the standard model of muscles, tendons, and ligamenta for virtual links and the origins, end points, and via-points of wires, the wires and the virtual links connected between the wires being used to express the muscles, the tendons, and the ligamenta. The processing section inputs (in step S103) from the new-body-model file stored in the storage section, the new-skeletal-model data which defines the new skeletal model given or measured in advance of the new body model by data for rigid links which express skeletal geometric shapes. Then, the processing section makes the input section arrange or automatically extracts a plurality of feature points on or from each rigid link according to the input standard-skeletal-model data (in step S105). The processing section also makes the input section arrange or automatically extracts a feature point corresponding to each feature point of the standard-skeletal-model data, on or from each rigid link according to the input new-skeletal-model data (in step S107), and associates the feature points of the obtained standard and new skeletal models with each other and stores them in the feature-point file.

When the processing section makes the input section arrange feature points, the operator, for example, appropriately specifies feature points or corresponding feature points on the screen of the display section by using input means of the input section, such as a pointing device, including a mouse or a pen for a touch-sensitive panel, while watching the standard and new skeletal models displayed on the display section. When the processing section automatically extracts feature points, the processing section appropriately selects the given number of points according to information determined in advance, such as the size, the arrangement, the direction, the position of the center of gravity, and others, in the rigid-link data. With the use of the method for extracting feature points from the standard skeletal model, the processing section can also appropriately select the given number of corresponding feature points in the new skeletal model according to information determined in advance, such as the size, the arrangement, the direction, the position of the center of gravity, and others, in the rigid-link data. It is also possible that the feature points of the standard-skeletal-model data is manually arranged and the feature points of the new-skeletal-model data is automatically extracted, and vice versa.

The processing section applies optimization calculation to a value corresponding to the sum of or the sum of the squares of the distances between the corresponding feature points to obtain the parameters of conversions which include parallel movement, rotational movement, and scaling, and stores the obtained conversion parameters into the conversion-parameter file (in step S109). Then, the processing section specifies a coordinate system for the input new skeletal model so as to fit the coordinate system of the standard skeletal model (in step S111). The processing section further maps the data of the standard model of muscles, tendons, and ligamenta for the virtual links and the positions of the origins, end points, and via-points of the wires in the standard skeletal model onto the new skeletal model according to the conversion parameters read from the conversion-parameter file to obtain data of the new model of muscles, tendons, and ligamenta for virtual links and the absolute positions of the origins, end points, and via-points of muscles, tendons, and ligamenta in the coordinate system of the new skeletal model, and stores the data into the new-body-model file (in step S113).

During or before the process of step S103, a step may be further included in which the processing section measures data for rigid links which express the skeletal geometric shape of the new skeletal model and writes the data into the new-body-model file stored in the storage section as new-skeletal-model data. In addition, the present embodiment can be applied to wire models having only origins and end points without via-points, and to models having no virtual links.

The steps S101 to S107, described above, are manually or automatically performed as pre-processing. Detailed processes in steps S109 to S113 will be described below.

(Optimization Calculation in Step S109)

Figure 23:
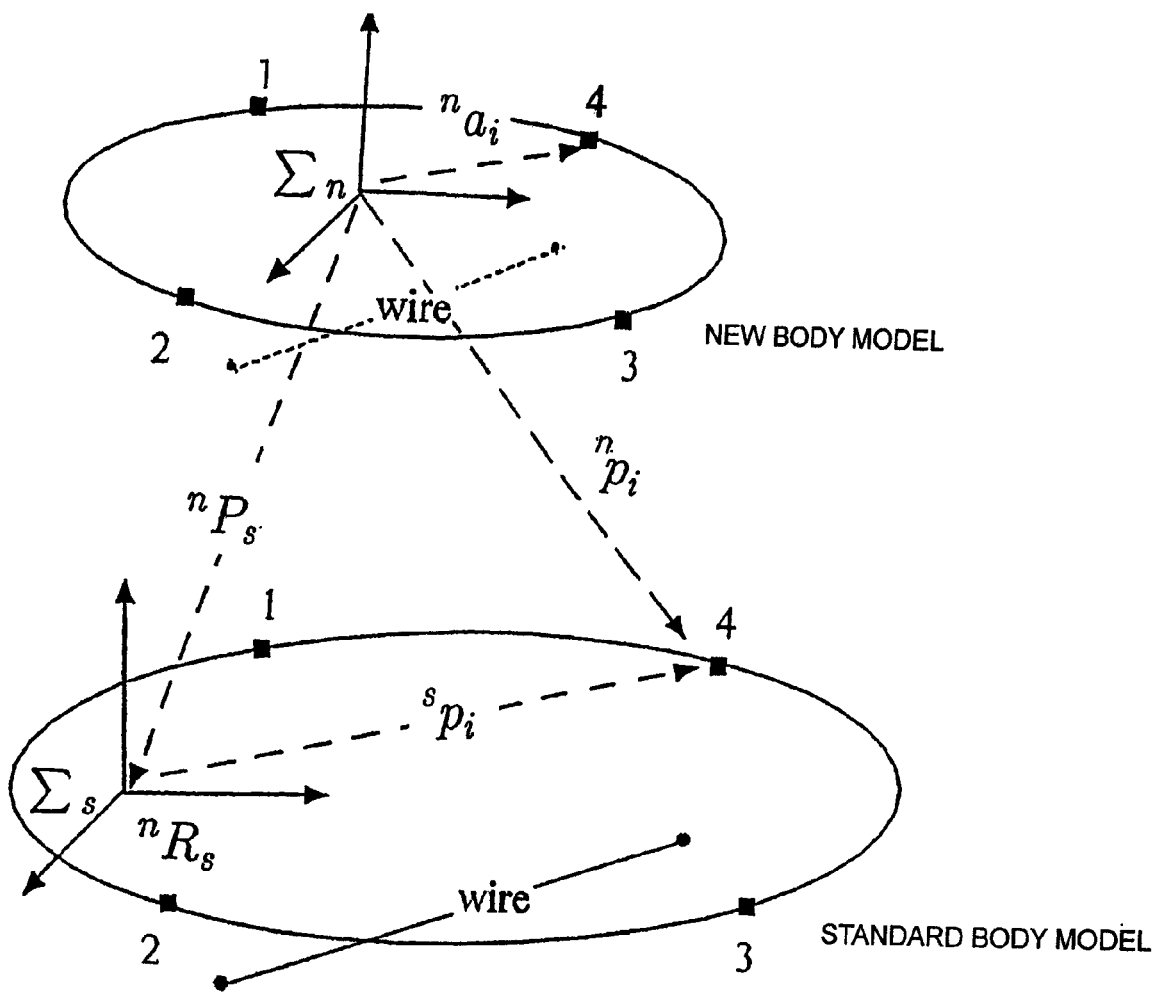
FIG. 23 is a view showing mapping from a standard body model (at a lower part) to a new body model (at an upper part)

FIG. 23 is a view showing mapping from the standard body model (shown at a lower part) to the new body model (shown at an upper part).

An optimization evaluation function J can, for example, be the sum of the squares of the distances between the corresponding feature points of the standard skeletal model and the new skeletal model, and be expressed as follows:

$$J(y) = \sum_i J_i, \quad J_i = \frac{1}{2}|{}^n p_i - {}^n a_i|^2$$

where ${}^n p_i$ indicates the position vector of a feature point i in the standard skeleton viewed from the coordinate system $\Sigma_n$ of the new skeletal model, and ${}^n a_i$ indicates the position of a feature point i in the new skeleton viewed from the coordinate system $\Sigma_n$ of the new skeletal model. The position vector of a feature point i in the standard skeleton viewed from the coordinate system $\Sigma_s$ of the standard skeletal model is expressed by ${}^s p_i = ({}^s p_{ix}\ {}^s p_{iy}\ {}^s p_{iz})^T$. ${}^n a_i$ and ${}^s p_i$ are constants.

An optimization parameter y is, for example, defined as a vector having a total of 14 variables, the variables of the position vector, ${}^n P_s = ({}^n p_{sx}\ {}^n p_{sy}\ {}^n p_{sz})^T$, from the origin of the coordinate system $\Sigma_n$ of the new skeletal model to the origin of the coordinate system $\Sigma_s$ of the standard skeletal model, the variables of the Euler parameter, $e = (e_0\ e_1\ e_2\ e_3)^T$, which expresses the rotation-conversion matrix ${}^n R_s$ from $\Sigma_n$ to $\Sigma_s$, the variables of the scale parameter, $s = (s_x\ s_y\ s_z)^T$, which expresses the size of the scale conversion between the coordinate systems $\Sigma_n$ and $\Sigma_s$, and the variables of the Euler parameter, $e_s = (e_{s0}\ e_{s1}\ e_{s2}\ e_{s3})^T$, which expresses the rotational-conversion matrix $R_s$ indicating the direction of the scale conversion.

$$y = ({}^n P_s^T e^T s^T e_s^T)^T$$

${}^n p_i$ can be expressed by the following equation by using ${}^n P_s$, ${}^n R_s$, and s.

$${}^n p_i = {}^n P_s + {}^n R_s {}^s p_i^x$$

where ${}^s p_i^x$ is the vector obtained by multiplying ${}^s p_i$ by a scale, and is expressed by the following expression.

$${}^s p_i^x = L {}^s p_i$$

Where $L = R_s^T \sum_s R_s$ $$R_s = R_s(e_s) = \begin{pmatrix} e_{s0}^2 - e_{s2}^2 - e_{s3}^2 & e_{s1}e_{s2} - 2e_{s0}e_{s3} & e_{s1}e_{s3} + 2e_{s0}e_{s2} \\ e_{s2}e_{s1} + 2e_{s0}e_{s3} & e_{s0}^2 - e_{s1}^2 - e_{s3}^2 & e_{s2}e_{s3} - 2e_{s0}e_{s1} \\ e_{s3}e_{s1} - 2e_{s0}e_{s2} & e_{s3}e_{s2} + 2e_{s0}e_{s1} & e_{s0}^2 - e_{s1}^2 - e_{s2}^2 \end{pmatrix}$$

$$\sum_s = \begin{pmatrix} s_x & 0 & 0 \\ 0 & s_y & 0 \\ 0 & 0 & s_z \end{pmatrix}$$

To optimize the evaluation function J of the above-described expression, standard optimization methods can be used, such as the down-hill method using the gradient of the evaluation function, genetic algorithm, the random search method, and a neural network. As an example, calculations in the down-hill method will be described below.

The partial differential of the evaluation function Ji for each feature point in terms of parameter y is expressed as follows since ${}^n a_i$ is a constant.

$$\frac{\partial J_i}{\partial y} = \frac{\partial J_i}{\partial {}^n p_i} \frac{\partial {}^n p_i}{\partial y} = ({}^n p_i - {}^n a_i)^T \begin{pmatrix} \frac{\partial {}^n p_{ix}}{\partial y_1} & \cdots & \frac{\partial {}^n p_{ix}}{\partial y_{10}} \\ \frac{\partial {}^n p_{iy}}{\partial y_1} & \cdots & \frac{\partial {}^n p_{iy}}{\partial y_{10}} \\ \frac{\partial {}^n p_{iz}}{\partial y_1} & \cdots & \frac{\partial {}^n p_{iz}}{\partial y_{10}} \end{pmatrix}$$

A method for calculating the second term at the right-hand side will be described below. The 3×3 matrix corresponding to the partial differential of ${}^n P_s$ in y is a unit matrix $1_3$.

The 3×4 matrix corresponding to the partial differential of e is calculated in the following way. Since ${}^n R_s$ can be expressed by the Euler parameter e by the following equation, $${}^n R_s = {}^n R_s(e) = \begin{pmatrix} e_0^2 - e_2^2 - e_3^2 & e_1 e_2 - 2e_0 e_3 & e_1 e_3 + 2e_0 e_2 \\ e_2 e_1 + 2e_0 e_3 & e_0^2 - e_1^2 - e_3^2 & e_2 e_3 - 2e_0 e_1 \\ e_3 e_1 - 2e_0 e_2 & e_3 e_2 + 2e_0 e_1 & e_0^2 - e_1^2 - e_2^2 \end{pmatrix}$$

the partial differentiation of e is a 3×4×3 tensor, and can be expressed by the following equation when each element thereof is expressed by three variable vectors enclosed in round parentheses.

$$E' = \frac{\partial {}^n R_s}{\partial e} = \begin{pmatrix} (2e_0, -2e_3, 2e_2) & (0, e_2, e_3) & (-2e_2, e_1, 2e_0) & (-2e_3, -2e_0, e_1) \\ (2e_3, 2e_0, -2e_1) & (e_2, -2e_1, -2e_0) & (e_1, 0, e_3) & (2e_0, -2e_3, e_2) \\ (-2e_2, 2e_1, 2e_1) & (e_3, 2e_0, -2e_1) & (-2e_0, e_3, -2e_2) & (e_1, e_2, 0) \end{pmatrix}$$

The partial differential of e is the following 3×4 matrix having as its elements the inner products of ${}^s p_i^x$ and each tensor element described above.

$$E_i = E' \times {}^s p_i^x$$

The partial differential of s can be expressed by the following equation.

$$S_i = {}^nR_s \frac{\partial^s p_i^\times}{\partial s}$$

The partial differential of $e_s$ can be expressed by the following equation.

$$E_{s_i} = {}^nR_s \frac{\partial^s p_i^\times}{\partial e_s}$$

The following equation is obtained from the above equations.

$$\frac{\partial^n p_i}{\partial y} = (I_3 E_i S_i E_{si})$$

For the following item obtained from the above, $$\frac{\partial J}{\partial y} = \sum_i \frac{\partial J_i}{\partial y}$$

$\Delta y$ is calculated with $1_4$ being set to a 4×4 unit matrix by the following equation, $$\Delta y = -kW \frac{\partial J}{\partial y}$$

Where $$W = \begin{pmatrix} I_3 & 0 & 0 & 0 \\ 0 & I_4 - ee^T & 0 & 0 \\ 0 & 0 & I_3 & 0 \\ 0 & 0 & 0 & I_4 - e_s e_s^T \end{pmatrix}$$

and the method of steepest descent is applied in which y is updated by $$y = y + \Delta y$$

until the evaluation function J shows no change. Then, y* which makes J minimum is obtained. This parameter gives the coordinate conversion which superpose the new skeletal model and the standard skeletal model most according to the given feature points. For subsequent calculation, ${}^n P_s$, ${}^n R_s$, s and $R_s$ corresponding to y* are indicated by ${}^n P^*_s$, ${}^n R^*_s$, s* and $R^*_s$, and L calculated by s* and $R^*_s$ is indicated by L*.

(Setting a Coordinate System for the New Skeletal Model in Step S111)

Figure 24:
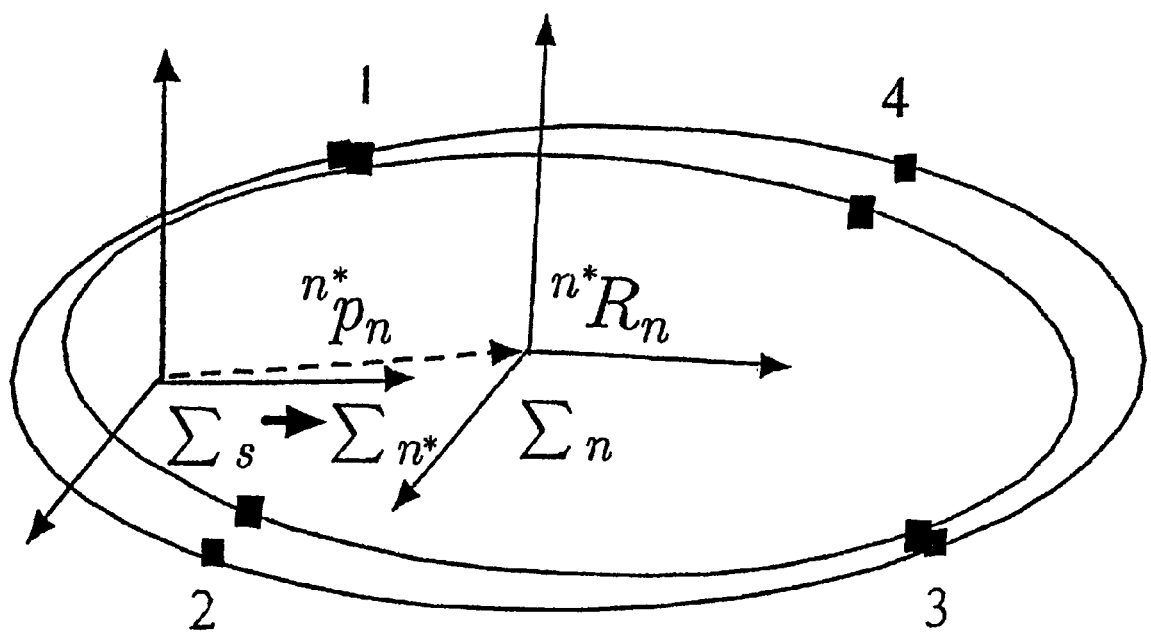
FIG. 24 is a view showing how to specify a coordinate system for a new skeletal model.

FIG. 24 is a view showing how to set a coordinate system for the new skeletal model.

The coordinate system $\Sigma_n$ for the new skeletal model is set to the position of the coordinate system for the standard body detailed model obtained when the optimization calculation is finished. Therefore, the position ${}^{n*}p_n$ and the posture ${}^{n*}R_n$ of $\Sigma_n$ viewed from $\Sigma_{n*}$ can be calculated by the following equations.

$${}^nR_n = {}^nR^*_s{}^T$$

$${}^np_n = -{}^{n*}R_n{}^np^*_s$$

The n coordinate system $\Sigma_n$ has been originally defined for the new skeletal model. Polygon data for the skeleton is defined in this coordinate system. The coordinate system $\Sigma_{n*}$ is the standard coordinate system $\Sigma_s$ obtained when the feature points are superposed (as a result of convergence calculation), and indicates a new coordinate system installed in the new skeletal model.

(Calculating the Positions of Origins, End Points, and Via-Points in the New Body Detailed Model in Step S113)

In this flowchart, the data of the standard model of muscles, tendons, and ligamenta, for the coordinates of the muscles, tendons, and ligamenta (having the origins and the end points (and via-points)) which have already existed in the standard skeletal model is newly defined in the new skeletal model in which data of the new model of muscles, tendons, and ligamenta, for the coordinates of the muscles, tendons, and ligamenta have not yet been defined. The coordinates of the muscles, tendons, and ligamenta are defined in the absolute coordinate system in the standard skeletal model (the origin can be specified at any appropriate position, such as the chest, waist, or navel).

It is assumed here that the origin of the coordinate system $\Sigma_s$ matches the origin of the coordinate system $\Sigma_{n*}$, and ${}^{n*}r_j$ and ${}^o r_j$ indicate the position in the coordinate system $\Sigma_n^*$ and the absolute position, of the origin, end point or a via-point whose position vector viewed from the coordinate system $\Sigma_s$ in the standard skeletal model is ${}^s r_j$. The conversion from ${}^s r_j$ to ${}^{n*}r_j$ is only scale conversion.

$${}^{n*}r_j = L^* \times {}^s r_j$$

The position ${}^o p_{n*}$ and the posture ${}^o R_{n*}$ of $\Sigma_{n*}$ in the absolute coordinate system are calculated from the position ${}^o p_n$ and the posture ${}^o R_n$ of $\Sigma_n$ in the absolute coordinate system by the following equations.

$${}^o p_{n*} = {}^o p_n + {}^o R_n {}^n P^*_s$$

$${}^o R_{n*} = {}^o R_n \times {}^n R^*_s$$

Therefore, the absolute position ${}^o r_j$ of the origin, end point, or via point is expressed by the following equation.

$${}^o r_j = {}^o p_{n*} + {}^o R_{n*} \times {}^{n*} r_j$$

4. Dynamics Model 4-1. Method for Generating a Model of Muscles, Tendons, and Ligamenta by Using Wires/Virtual Links.

A method for generating a model of muscles, tendons, and ligamenta by using wires/virtual links is the same as the modeling method described in A. 2-1.

4-2. Method for Describing the Model in VRML Format

The method for describing the model in VRML format is the same as the description method explained in A. 1-3.

C. Additional Description

A dynamics-model calculation method, a dynamics-model calculation apparatus, a dynamics-model calculation system according to the present invention can be provided by a dynamics-model calculation processing program for making a computer execute each step thereof, a computer-readable recording medium having recorded thereon the dynamics-model calculation processing program, a program product which can be loaded to an internal memory of a computer, the program product including the dynamics-model calculation processing program, a computer which includes the program, such as a server, and others.

A body-model generation method, a body-model generation apparatus, a body-model generation system according to the present invention can be provided by a body-model generation processing program for making a computer execute each step thereof, a computer-readable recording medium having recorded thereon the body-model generation processing program, a program product which can be loaded to an internal memory of a computer, the program product including the body-model generation processing program, a computer which includes the program, such as a server, and others.

INDUSTRIAL APPLICABILITY

According to the present invention, a human-body detailed model having geometric data of bones and data of muscles, tendons, and ligamenta can be generated by commercially available modeling software. By storing the detailed model in a file with the use of a method according to the present invention, a great number of models can be stored in a data base, or can be shared by a plurality of applications.

In addition, according to the present invention, forward-dynamics calculation (calculating motion from muscular strength) and inverse-dynamics calculation (calculating muscular strength and ligamental strength required for motion) can be performed at high speed for a human-body detailed model having geometric data of bones and data of muscles, tendons, and ligamenta.

Further, according to the present invention, as described above, when a new geometric model of bones is given, mapping between the new model and a standard body model defined in advance which indicates a standard body can be obtained to provide a body-model generation method, a body-model generation program, a recording medium having stored thereon the generation program, and a recording medium having recorded thereon body-model data, for automatically generating a new body model.

The invention claimed is:

1. A body-model generation method for generating, according to a standard body model which expresses a skeletal model and a model of muscles, tendons, and ligamenta of a standard body which includes a human body, a living body, or an animal body, a new body model by mapping the model of muscles, tendons, and ligamenta onto a new skeletal model which expresses the skeleton of a new body, said method implemented by a system including a processing device, a storage device and an input device, said method comprising:
   a step of inputting by the processing device from a standard-body-model file stored in the storage device, standard-body-model data which defines the standard body model by standard-skeletal-model data for rigid links expressing the geometric shape of a skeleton, and standard-model data for muscles, tendons, and ligamenta, when the muscles, tendons, and ligamenta are expressed by wires and virtual links connected between the wires, for the virtual links and the origins, end points, and via-points of the wires;
   a step of inputting by the processing device from a new-body-model file stored in the storage device, new-skeletal-model data which defines the new skeletal model measured or given in advance of the new body model, by data for the rigid links expressing the geometric shape of the skeleton;
   a step of making the input device arrange or automatically extracting a plurality of feature points on or from each rigid link according to the input standard-skeletal-model data, by the processing device;
   a step of making the input device arrange or automatically extracting a feature point corresponding to each feature point of the standard-skeletal-model data on or from each rigid link according to the input new-skeletal-model data, by the processing device;
   a step of associating the obtained feature points of the standard-skeletal-model data with the obtained feature points of the new-skeletal-model data and storing them in a feature-point file, by the processing device;
   a step of applying optimization calculation to a value corresponding to the sum of or the sum of the squares of the distances between the corresponding feature points to obtain the parameters of conversions which include parallel movement, rotational movement, and scaling, and of storing the conversion parameters into a conversion-parameter file, by the processing device;
   a step of specifying a coordinate system for the input new skeletal model so as to fit the coordinate system of the standard skeletal model, by the processing device; and
   a step of mapping the data of the standard model of muscles, tendons, and ligamenta for the virtual links and the positions of the origins, the end points, and via-points of the wires in the standard skeletal model onto the new skeletal model according to the conversion parameters read from the conversion-parameter file to obtain data of the new model of muscles, tendons, and ligamenta for virtual links and the absolute positions of the origins, end points, and via-points of muscles, tendons, and ligamenta in the coordinate system of the new skeletal model, and of storing the data into the new-body-model file, by the processing device.

2. A body-model generation method according to claim 1, further comprising a step of measuring data for the rigid links which express the geometric shape of the skeleton of the new skeletal model, and of storing the data into the new-body-model file stored in the storage device as new-skeletal-model data, by the processing device.

3. A body-model generation method according to claim 1, wherein the conversion parameters are defined by vectors $(^nP_s{}^T e^T s^T e_s{}^T)$ which comprises a position vector, $^nP_s = (^nP_{sx}\, ^nP_{sy}\, ^nP_{sz})^T$, from the origin of the coordinate system $\Sigma_n$ of the new skeleton model to the origin of the coordinate system $\Sigma_s$ of the standard skeleton model, an Euler parameter, $e = (e_0 e_1 e_2 e_3)^T$, which expresses the rotation-conversion matrix $^nR_s$ from $\Sigma_n$ to $\Sigma_s$, a scale parameter, $s = (s_x s_y s_z)^T$, which expresses the size of the scale conversion between the coordinate systems $\Sigma_n$ and $\Sigma_s$, and an Euler parameter, $e_s = (e_{s0} e_{s1} e_{s2} e_{s3})_T$, which expresses the rotational-conversion matrix $R_s$ indicating the direction of the scale conversion.

4. A body-model generation method according to claim 1, wherein the data for the wires and/or the virtual links is data of any one of the following models,
   model in which one part is replaced with one simple wire formed of only an origin and an end point,
   model in which one part is replaced with one wire formed of an origin, a via-point, and an end point,
   model in which one part is replaced with a plurality of wires,
   model in which one part is replaced with a virtual link and a plurality of wires, and
   compound model.

5. A body-model generation method according to claim 1, wherein
   the skeletal-model data defines rigid links a plurality of which is coupled by joints which express joints having a plurality of degrees of freedom to form a skeleton;
   the data of the model for muscles, tendons, and ligaments express wires which connect origins and end points secured to predetermined locations of bones expressed by the rigid links, pass through no or one or more via-points which allow sliding and are secured to bones, and are formed such that the lengths and tension of the wires can be changed according to the movement of the rigid links, and virtual links which are formed such that the origins and end points of a plurality of the wires are secured; and the standard body model and the new body model are generated such that forces applied to the wires and the virtual links, the lengths of the wires, and the motion of the rigid links interact with each other.

6. A body-model generation method according to claim 5, wherein the rigid links are defined by shape data and dynamics data;
the wires are defined by position data of edge points and/or a via-point; and
the virtual links are defined by shape data and dynamics data.

7. A body-model generation method for generating, according to a standard body model which expresses a skeletal model and a model of muscles, tendons, and ligamenta of a standard body which includes a human body, a living body, or an animal body, a new body model by mapping the model of muscles, tendons, and ligamenta onto a new skeletal model which expresses the skeleton of a new body, said method implemented by a system including a processing device, a storage device and an input device, said method comprising:

a step of inputting by the processing device from a standard-body-model file stored in the storage device, standard-body-model data which defines the standard body model by standard-skeletal-model data for rigid links expressing the geometric shape of a skeleton, and standard-model data for muscles, tendons, and ligamenta, when the muscles, tendons, and ligamenta are expressed by wires, for the origins, end points, and via-points or for the origins and end points of the wires;

a step of inputting by the processing device from a new-body-model file stored in the storage device, new-skeletal-model data which defines the new skeletal model measured or given in advance of the new body model, by data for the rigid links expressing the geometric shape of the skeleton;

a step of making the input device arrange or automatically extracting a plurality of feature points on or from each rigid link according to the input standard-skeletal-model data, by the processing device;

a step of making the input device arrange or automatically extracting a feature point corresponding to each feature point of the standard-skeletal-model data on or from each rigid link according to the input new-skeletal-model data, by the processing device;

a step of associating the obtained feature points of the standard-skeletal-model data with the obtained feature points of the new-skeletal-model data and storing them in a feature-point file, by the processing device;

a step of applying optimization calculation to a value corresponding to the sum of or the sum of the squares of the distances between the corresponding feature points to obtain the parameters of conversions which include parallel movement, rotational movement, and scaling, and of storing the conversion parameters into a conversion-parameter file, by the processing device;

a step of specifying a coordinate system for the input new skeletal model so as to fit the coordinate system of the standard skeletal model, by the processing device; and a step of mapping the data of the standard model of muscles, tendons, and ligamenta for the positions of the origins, end points, and via-points, or the origins and end points of the wires in the standard skeletal model onto the new skeletal model according to the conversion parameters read from the conversion-parameter file to obtain data of the new model of muscles, tendons, and ligamenta for the absolute positions of the origins, end points, and via-points, or the origins and the end points of muscles, tendons, and ligamenta in the coordinate system of the new skeletal model, and of storing the data into the new-body-model file, by the processing device.

8. A body-model generation method according to claim 7, further comprising a step of measuring data for the rigid links which express the geometric shape of the skeleton of the new skeletal model, and of storing the data into the new-body-model file stored in the storage device as new-skeletal-model data, by the processing device.

9. A body-model generation method according to claim 7, wherein the conversion parameters are defined by vectors $({}^n P_s{}^T e^T s^T e_s{}^T)$ which comprises a position vector, ${}^n P_s = ({}^n P_{sx} {}^n P_{sy} {}^n P_{sz})^T$, from the origin of the coordinate system $\Sigma_n$ of the new skeleton model to the origin of the coordinate system $\Sigma_s$ of the standard skeleton model, an Euler parameter, $e = (e_0 e_1 e_2 e_3)^T$, which expresses the rotation-conversion matrix ${}^n R_s$ from $\Sigma_n$ to $\Sigma_s$, a scale parameter, $s = (s_x s_y s_z)^T$, which expresses the size of the scale conversion between the coordinate systems $\Sigma_n$ and $\Sigma_s$, and an Euler parameter, $e_s = (e_{s0} e_{s1} e_{s2} e^{s3})^T$, which expresses the rotational-conversion matrix $R_s$ indicating the direction of the scale conversion.

10. A body-model generation method according to claim 7, wherein the data for the wires and/or the virtual links is data of any one of the following models, model in which one part is replaced with one simple wire formed of only an origin and an end point, model in which one part is replaced with one wire formed of an origin, a via-point, and an end point, model in which one part is replaced with a plurality of wires, model in which one part is replaced with a virtual link and a plurality of wires, and compound model.

11. A body-model generation method according to claim 7, wherein the skeletal-model data defines rigid links a plurality of which is coupled by joints which express joints having a plurality of degrees of freedom to form a skeleton;

the data of the model for muscles, tendons, and ligaments express wires which connect origins and end points secured to predetermined locations of bones expressed by the rigid links, pass through no or one or more via-points which allow sliding and are secured to bones, and are formed such that the lengths and tension of the wires can be changed according to the movement of the rigid links, and virtual links which are formed such that the origins and end points of a plurality of the wires are secured; and the standard body model and the new body model are generated such that forces applied to the wires and the virtual links, the lengths of the wires, and the motion of the rigid links interact with each other.

12. A computer-readable recording medium having stored a body-model generation program for making a computer execute each of the forgoing steps, for generating, according to a standard body model which expresses a skeletal model and a model of muscles, tendons, and ligamenta of a standard body which includes a human body, a living body, or an animal body, a new body model by mapping the model of muscles, tendons, and ligamenta onto a new skeletal model which expresses the skeleton of a new body, said computer including a processing device, a storage device and an input device, said steps comprising:

a step of inputting by the processing device from a standard-body-model file stored in the storage device, standard-body-model data which defines the standard body model by standard-skeletal-model data for rigid links expressing the geometric shape of a skeleton, and standard-model data for muscles, tendons, and ligamenta, when the muscles, tendons, and ligamenta are expressed by wires and virtual links connected between the wires, for the virtual links and the origins, end points, and via-points of the wires;

a step of inputting by the processing device from a new-body-model file stored in the storage device, new-skeletal-model data which defines the new skeletal model measured or given in advance of the new body model, by data for the rigid links expressing the geometric shape of the skeleton;

a step of making the input device arrange or automatically extracting a plurality of feature points on or from each rigid link according to the input standard-skeletal-model data, by the processing device;

a step of making the input device arrange or automatically extracting a feature point corresponding to each feature point of the standard-skeletal-model data on or from each rigid link according to the input new-skeletal-model data, by the processing device;

a step of associating the obtained feature points of the standard-skeletal-model data with the obtained feature points of the new-skeletal-model data and storing them in a feature-point file, by the processing device;

a step of applying optimization calculation to a value corresponding to the sum of or the sum of the squares of the distances between the corresponding feature points to obtain the parameters of conversions which include parallel movement, rotational movement, and scaling, and of storing the conversion parameters into a conversion-parameter file, by the processing device;

a step of specifying a coordinate system for the input new skeletal model so as to fit the coordinate system of the standard skeletal model, by the processing device; and a step of mapping the data of the standard model of muscles, tendons, and ligamenta for the virtual links and the positions of the origins, the end points, and via-points of the wires in the standard skeletal model onto the new skeletal model according to the conversion parameters read from the conversion-parameter file to obtain data of the new model of muscles, tendons, and ligamenta for virtual links and the absolute positions of the origins, end points, and via-points of muscles, tendons, and ligamenta in the coordinate system of the new skeletal model, and of storing the data into the new-body-model file, by the processing device.

13. A computer-readable recording medium having stored a body-model generation program for making a computer execute each of the forgoing steps, for generating, according to a standard body model which expresses a skeletal model and a model of muscles, tendons, and ligamenta of a standard body which includes a human body, a living body, or an animal body, a new body model by mapping the model of muscles, tendons, and ligamenta onto a new skeletal model which expresses the skeleton of a new body, said computer including a processing device, a storage device and an input device, said steps comprising:

a step of inputting by the processing device from a standard-body-model file stored in the storage device, standard-body-model data which defines the standard body model by standard-skeletal-model data for rigid links expressing the geometric shape of a skeleton, and standard-model data for muscles, tendons, and ligamenta, when the muscles, tendons, and ligamenta are expressed by wires, for the origins, end points, and via-points or for the origins and end points of the wires;

a step of inputting by the processing device from a new-body-model file stored in the storage device, new-skeletal-model data which defines the new skeletal model measured or given in advance of the new body model, by data for the rigid links expressing the geometric shape of the skeleton;

a step of making the input device arrange or automatically extracting a plurality of feature points on or from each rigid link according to the input standard-skeletal-model data, by the processing device;

a step of making the input device arrange or automatically extracting a feature point corresponding to each feature point of the standard-skeletal-model data on or from each rigid link according to the input new-skeletal-model data, by the processing device;

a step of associating the obtained feature points of the standard-skeletal-model data with the obtained feature points of the new-skeletal-model data and storing them in a feature-point file, by the processing device;

a step of applying optimization calculation to a value corresponding to the sum of or the sum of the squares of the distances between the corresponding feature points to obtain the parameters of conversions which include parallel movement, rotational movement, and scaling, and of storing the conversion parameters into a conversion-parameter file, by the processing device;

a step of specifying a coordinate system for the input new skeletal model so as to fit the coordinate system of the standard skeletal model, by the processing device; and a step of mapping the data of the standard model of muscles, tendons, and ligamenta for the positions of the origins, end points, and via-points, or the origins and end points of the wires in the standard skeletal model onto the new skeletal model according to the conversion parameters read from the conversion-parameter file to obtain data of the new model of muscles, tendons, and ligamenta for the absolute positions of the origins, end points, and via-points, or the origins and the end points of muscles, tendons, and ligamenta in the coordinate system of the new skeletal model, and of storing the data into the new-body-model file, by the processing device.

14. A computer-readable recording medium having stored thereon a standard-body-model data used for generating, according to a standard body model which expresses a skeletal model and a model of muscles, tendons, and ligamenta of a standard body which includes a human body, a living body, or an animal body, a new body model by mapping the model of muscles, tendons, and ligamenta onto a new skeletal model which expresses the skeleton of a new body, the standard-body-model data having a standard-skeletal-model data structure for rigid links expressing the geometric shape of a skeleton, and a standard-model data structure for muscles, tendons, and ligamenta, when the muscles, tendons, and ligamenta are expressed by wires and virtual links connected between wires, for the virtual links and the origins, end points, and via-points of the wires, and defining the standard body model, and a processing device (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the virtual links and the positions of the origins, end points, and via-points of the wires in the standard skeletal model onto the new skeletal model to obtain data of the new model of muscles, tendons, and ligamenta for virtual links and the origins, end points, and via-points of muscles, tendons, and ligamenta in the coordinate system of the new skeletal model.

15. A computer-readable recording medium having stored thereon a standard-body-model data used for generating, according to a standard body model which expresses a skeletal model and a model of muscles, tendons, and ligamenta of a standard body which includes a human body, a living body, or an animal body, a new body model by mapping the model of muscles, tendons, and ligamenta onto a new skeletal model which expresses the skeleton of a new body, the standard-body-model data having a standard-skeletal-model data structure for rigid links expressing the geometric shape of a skeleton, and a standard-model data structure for muscles, tendons, and ligamenta, when the muscles, tendons, and ligamenta are expressed by wires, for the origins, end points, and via-points, or for the origins and end points of the wires, and defining the standard body model, and a processing device (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the positions of the origins, end points, and via-points, or the origins and end-points of the wires in the standard skeletal model onto the new skeletal model to obtain data of the new model of muscles, tendons, and ligamenta for the origins, end points, and via-points, or the origins and end points of muscles, tendons, and ligamenta in the coordinate system of the new skeletal model.

16. A computer-readable recording medium having stored thereon a new-body-model data generated by mapping, according to a standard body model which expresses a skeletal model and a model of muscles, tendons, and ligamenta of a standard body which includes a human body, a living body, or an animal body, the model of muscles, tendons, and ligamenta onto a new skeletal model which expresses a new body, the new-body-model data having a standard-skeletal-model data structure for rigid links expressing the geometric shape of a skeleton, and a new-model data structure for muscles, tendons, and ligamenta, when the muscles, tendons, and ligamenta are expressed by wires and virtual links connected between the wires, for the virtual links and the origins, end points, and via-points of the wires, and defining a new body model, the standard-body-model data defining the standard body model by a standard-skeletal-model data for rigid links expressing the geometric shape of a skeleton, and a standard-model data structure for muscles, tendons, and ligamenta, when the muscles, tendons, and ligamenta are expressed by wires and virtual links connected between the wires, for the virtual links and the origins, end points, and via-points of the wires, and a processing device (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the virtual links and the positions of the origins, end points, and via-points of the wires in the standard skeletal model onto the new skeletal model to obtain data of the new model of muscles, tendons, and ligamenta for virtual links and the origins, end points, and via-points of muscles, tendons, and ligamenta in the coordinate system of the new skeletal model to generate the new-body-model data.

17. A computer-readable recording medium having stored thereon a new-body-model data generated by mapping, according to a standard body model which expresses a skeletal model and a model of muscles, tendons, and ligamenta of a standard body which includes a human body, a living body, or an animal body, the model of muscles, tendons, and ligamenta onto a new skeletal model which expresses a new body, the new-body-model data having a standard-skeletal-model data structure for rigid links expressing the geometric shape of a skeleton, and a new-model data structure for muscles, tendons, and ligamenta, when the muscles, tendons, and ligamenta are expressed by wires, for the origins, end points, and via-points, or for the origins and end points of the wires, and defining a new body model, the standard-body-model data defining the standard body model by a standard-skeletal-model data for rigid links expressing the geometric shape of a skeleton, and a standard-model data structure for muscles, tendons, and ligamenta, when the muscles, tendons, and ligamenta are expressed by wires, for the origins, end points, and via-points, or for the origins and end points of the wires, and a processing device (a) applying optimization calculation to a value corresponding to the sum of or the sum of the squares of the distances between feature points of the rigid links of the standard-skeletal-model data and corresponding feature points of the new-skeletal-model data defined by data for the rigid links of the new body model to obtain the parameters of conversions which include parallel movement, rotational movement, and scaling, and (b) specifying a coordinate system for the input new skeletal model so as to fit the coordinate system of the standard skeletal model according to the obtained conversion parameters and mapping the data of the standard model of muscles, tendons, and ligamenta for the positions of the origins, end points, and via-points, or the origins and end points of the wires in the standard skeletal model onto the new skeletal model to obtain data of the new model of muscles, tendons, and ligamenta for the origins, end points, and via-points, or the origins and end points of muscles, tendons, and ligamenta in the coordinate system of the new skeletal model to generate the new-body-model data.

* * * * *